United States Patent [19]

Bieniarz et al.

[11] Patent Number: 4,978,613

[45] Date of Patent: Dec. 18, 1990

[54] BETA-LACTAMASE ASSAY EMPLOYING CHROMOGENIC PRECIPITATING SUBSTRATES

[75] Inventors: Christopher Bieniarz, Highland Park; Michael J. Cornwell; Douglas F. Young, both of Lake Villa, all of Ill.

[73] Assignee: Abbott Laboratories, Abbott Park, Ill.

[21] Appl. No.: 298,098

[22] Filed: Jan. 17, 1989

[51] Int. Cl.$^5$ ............................................. C12Q 1/34
[52] U.S. Cl. .......................................... 435/18; 435/4
[58] Field of Search ........................................... 435/18

[56] References Cited

PUBLICATIONS

Dojin–Chem. Abst., vol. 101 (1984), p. 186950s.
Tanaka et al.–Chem. Abst., vol. 104 (1986), p. 203469y.
Osokina et al.–Chem. Abst., vol. 105 (1986), p. 111915h.
Wielinger et al.–Chem. Abst., vol. 99 (1983), p. 152,073h.

*Primary Examiner*—Sam Rosen
*Attorney, Agent, or Firm*—James D. McNeil; Priscilla E. Porembski

[57] ABSTRACT

A method for detecting $\beta$-lactamases which may be present in a sample by using a disclosed chromogenic precipitating substrate. A sample is exposed to a disclosed $\beta$-lactamase substrate and a colored precipitate forms in the presence of an active $\beta$-lactamase.

23 Claims, 1 Drawing Sheet

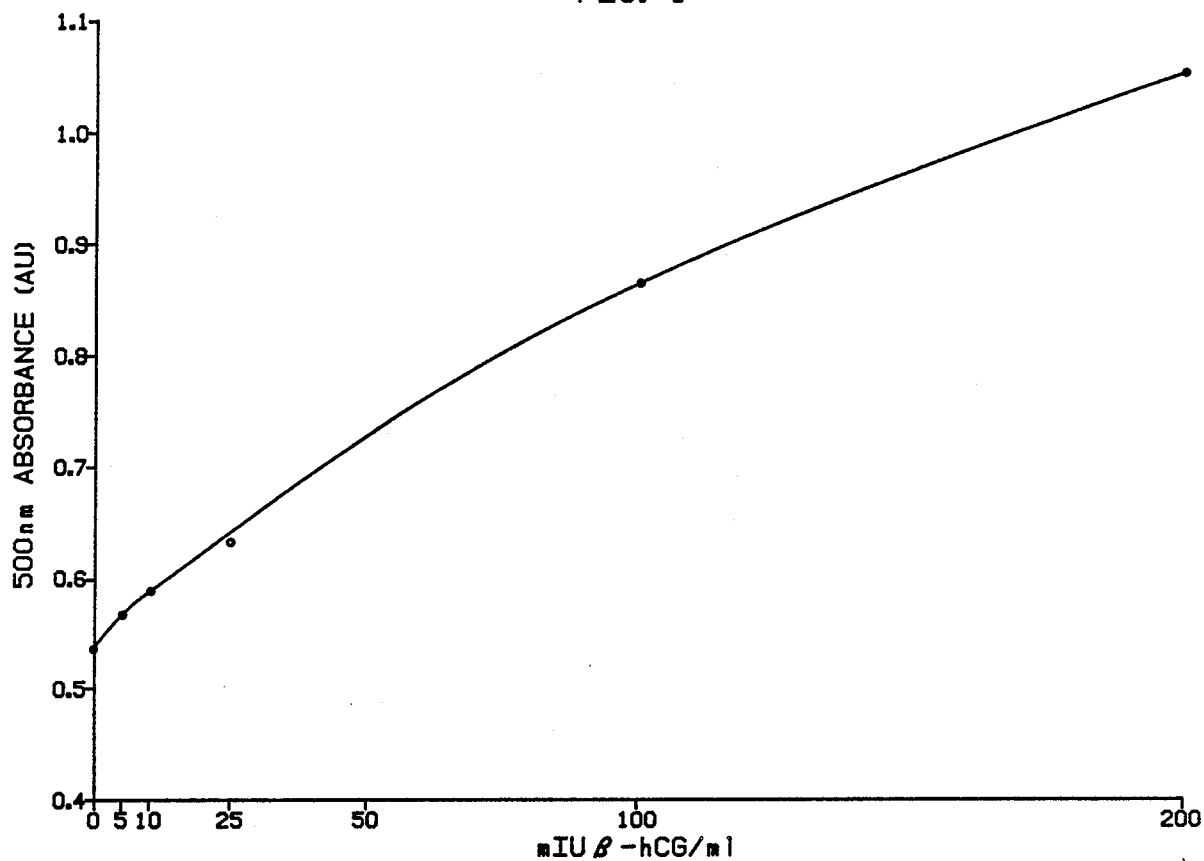

BETA-LACTAMASE ASSAY EMPLOYING CHROMOGENIC PRECIPITATING SUBSTRATES

BACKGROUND OF THE INVENTION

1. Technical Field

This invention relates to assays employing chromogenic reactions in which one of the reagents is a cephalosporin substrate of β-lactamase.

2. Description of Related Art

β-lactamases are enzymes produced by certain bacteria. These enzymes confer on these bacteria resistance to β-lactam antibiotic therapy. The capacity to produce β-lactamase is probably the most important and common cause of resistance to β-lactam antibiotics in bacteria. For instance, if a patient infected with bacteria producing β-lactamase is treated with cephalosporin, many β-lactamases will recognize the cephalosporin and convert it into a metabolite with little or no antibiotic potency. Screening patient samples for β-lactamase activity can avoid subjecting the patient to a course of therapy with inappropriate antibiotics.

β-lactamases also have uses as a label in enzyme immunoassays (EIAs). β-lactamases have very high turnover numbers, are easily available in high purity from many commercial sources, have pH optima compatible with ligand-antibody binding, are relatively stable, have low molecular weight, are inexpensive, and are usually absent in body fluids.

By contrast, other commonly used enzyme labels such as alkaline phosphatase, horseradish peroxidase, and β-galactosidase do not have all of these advantages in common. For instance, horseradish peroxidase requires chromogenic substrates unstable to varying degrees in the presence of hydrogen peroxide, and immunogenicity and mutagenicity of the chromogenic substrates for horseradish peroxidase are potential problems. Another disadvantage is the low yield of the horseradish peroxidase/IgG conjugation and loss of enzyme activity after conjugation. Furthermore, horseradish peroxidase exhibits markedly different stability characteristics at different pH values. Horseradish peroxidase is also difficult to use because of hemolysis problems and cross-reactivity of its substrates with hemoglobin.

β-galactosidase substrates are often subjected to high rates of non-enzymatic hydrolysis leading to high numbers of failed tests. In addition, a loss of enzymatic activity upon enzyme conjugation can occur. Finally, the high molecular weight of β-galactosidase presents problems in some applications. As a result, few if any commercial products exist utilizing β-galactosidase.

Alkaline phosphatase is a readily available enzyme at reasonable cost. However, the efficiency of conjugation of alkaline phosphatase is rather low, typically about 5 percent, and after conjugation, only about 10 percent or less of the immunological activity of the ligand conjugated to alkaline phosphatase remains. Thermal stability of the conjugates of alkaline phosphotase is typically very low. Furthermore, because many samples from humans contain alkaline phosphatase, it is difficult to detect the labelled alkaline phosphatase from the endogenous alkaline phosphatase activity.

SUMMARY OF THE INVENTION

The present invention is a method and kit for the detection of β-lactamase enzymes in samples containing certain infectious bacteria, as well as for enzyme immunoassays which use β-lactamase as a label. The method of the present invention includes detecting β-lactamase activity in a sample by exposing the sample to a β-lactamase substrate of formula I

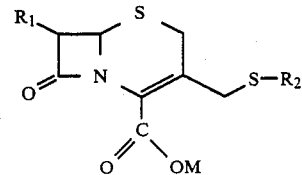

$R_1$ is a group which maintains the ability of the cephalosporin substrate I to be recognized by β-lactamase. When the compound is exposed to a β-lactamase, the $R_2$ group, together with the sulfur atom to which it is attached, form a leaving group the conjugate acid of which has a pKa in water of less than 8. M is hydrogen or a group I metal. After the β-lactamase-containing sample is exposed to a compound of formula I and the leaving group is generated, the leaving group is exposed to a tetrazolium salt of formula II

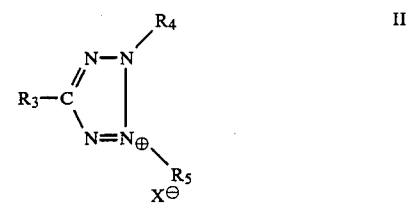

wherein $R_3$, $R_4$ and $R_5$ are independently selected from groups such that the redox potential of the resulting tetrazolium salt is 0 or lower volts. X is an anion.

When the leaving group of substrate I is exposed to the tetrazolium salt, a colored precipitate of formazan is formed in the presence of the leaving group which indicates that the sample contains a β-lactamase enzyme.

The current invention also involves kits for the detection of βlactamase in samples and assays which employ β-lactamase as labels.

DETAILED DESCRIPTION OF THE INVENTION

General

Figure 1:
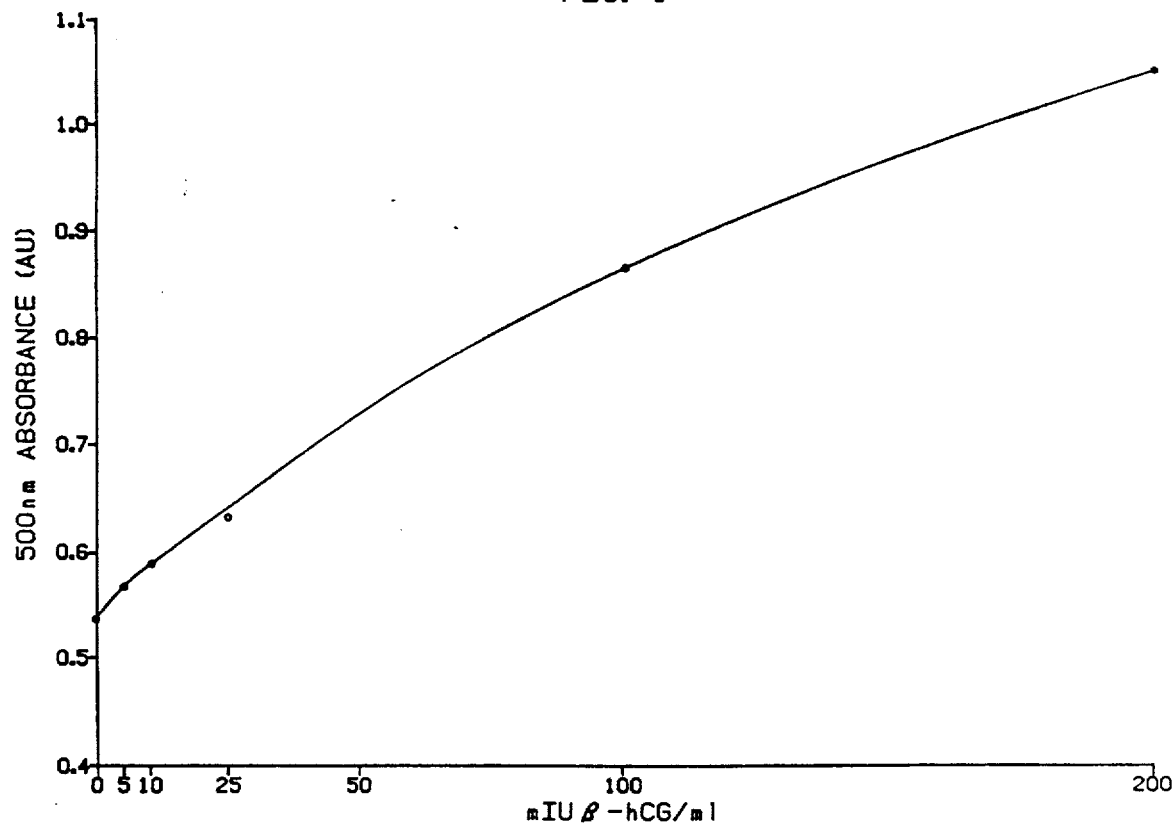
FIG. 1 is a standard curve obtained when using reagents of this invention in an assay for β-hCG.

This invention involves kits and methods for the detection of β-lactamases. Preferred enzymes detected by the claimed method and kit are a subclass of β-lactamases designated as cephalosporinases. The claimed kits and method involve exposing the enzyme to cephalosporins of formula I in the presence of the tetrazolium salt of formula II as illustrated in the reaction scheme below: The β-lactamase cleaves the lactam ring in substrate I to create an intermediate compound IA which produces a leaving group of formula III. The leaving group reacts with the tetrazolium salt of formula II to produce a colored precipitate of formazan (Formula IV), indicating the presence or quantity of β-lactamase.

R₁ Definition

R₁, as indicated above, is a group which maintains the ability of the substrate of formula I to be recognized as a substrate by β-lactamases and cleave the β-lactam ring. R₁ can be a substituted or unsubstituted phenyl group linked to the lactam ring by an acetamide group, a substituted or unsubstituted alicyclic hydrocarbon group linked to the lactam ring by an acetamide group, or a substituted or unsubstituted straight or branched aliphatic hydrocarbon chain linked to the lactam ring by an acetamide group. Appropriate substituents for the groups above include halogen, cyano, sulfoxy or sulfonyl group(s).

R₁ can also be an amino, substituted or unsubstituted alkylamino, substituted or unsubstituted arylamino group, or substituted or unsubstituted aromatic or non-aromatic heterocyclic substituted amino group. Alkylamino or arylamino groups can be substituted with either an aliphatic straight or branched chain or an alicyclic group.

R₁ can also be a group of the formula:

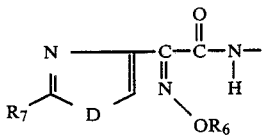

where R₆ is a lower aliphatic group, and R₇ is an amino or alkylamino group, and D represents an oxygen or sulfur atom. R₁ can also be a group of the formula:

where R₈ is a 4–6 membered heterocyclic ring.

Preferred groups for R₁ include those of the formulae:

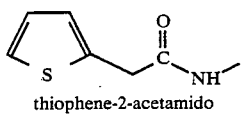
thiophene-2-acetamido

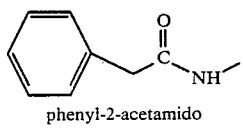
phenyl-2-acetamido

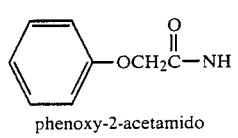
phenoxy-2-acetamido

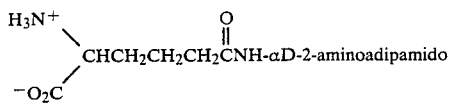
CHCH₂CH₂CH₂CNH-αD-2-aminoadipamido

-continued

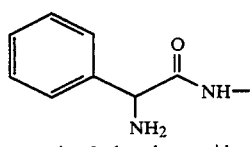
2-amino-2-phenylacetamido

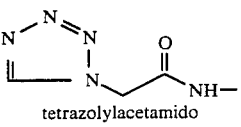
tetrazolylacetamido

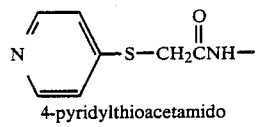
4-pyridylthioacetamido

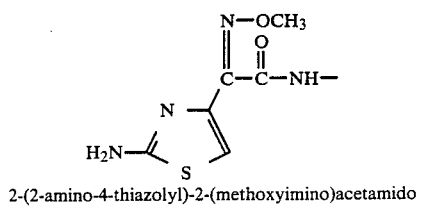
2-(2-amino-4-thiazolyl)-2-(methoxyimino)acetamido

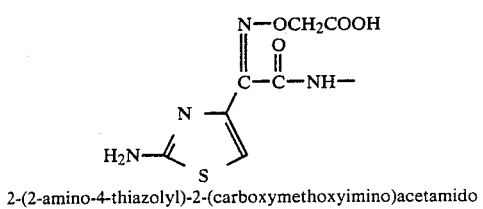
2-(2-amino-4-thiazolyl)-2-(carboxymethoxyimino)acetamido

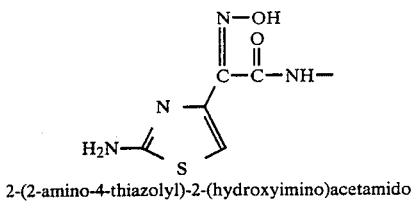
2-(2-amino-4-thiazolyl)-2-(hydroxyimino)acetamido

R₁ also includes alkoxycarbonyl, halogen, cyano, sulfoxy, or aminosulfonyl.

This is only a representative list of the possible R₁ substituents. With reasonable experimentation, those of ordinary skill will find other R₁ substituents which will preserve the ability of the compound of formula I to serve as a substrate for β-lactamase for cephalosporins.

R₂ Definition

As indicated above, R₂ forms a leaving group with the sulfur atom to which it is attached. As a consequence of the β-lactamase catalyzed β-lactam ring cleavage, the leaving group is released into solution. The conjugate acid of the leaving group must have a pKa of less than about ten such that the tetrazolium salt of formula II can be reduced to produce a colored precipitate of formazan of Formula IV above. The reduction of tetrazolium salts to colored formazans by the leaving group is pH dependent, and is facilitated by the increase of pH of the solution. Thus since the reductions are carried at pH 6.0–9.0, preferably pH 7.0, the best leaving groups are those significantly deprotonated in the aforesaid pH range, e.g., thiols having pKa 8 or lower. Naturally this requirement will suggest a wide variety of leaving groups to those of ordinary skill in the art which can be ascertained with reasonable experimentation. Preferred leaving groups include an aliphatic or aromatic thiol; halo or amino substituted thiophenol; hydroxy, halo, or amino substituted mercapto pyridines; aliphatic or aromatic thiol acids; thiosulfonic acids; or a mercapto amino acid. Such preferred leaving groups include p-bromo-thiophenol, p-amino-thiophenol, 2-mercapto-3 pyridinol, thiolacetic acid, thiobenzoic acid, or cysteine.

$R_3$–$R_5$ Definition $R_3$–$R_5$ are independently selected from groups such that the redox potential

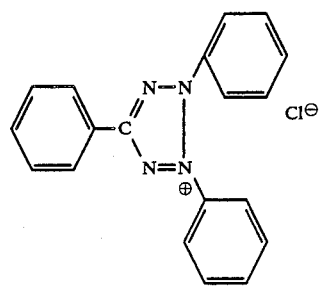

2,3,5-triphenyl-2H-tetrazolium chloride (TTC)

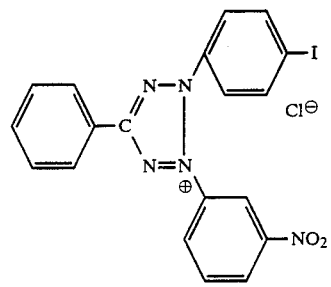

2-p-iodophenyl-3-p-nitrophenyl-5-phenyl-2H-tetrazolium chloride (INT)

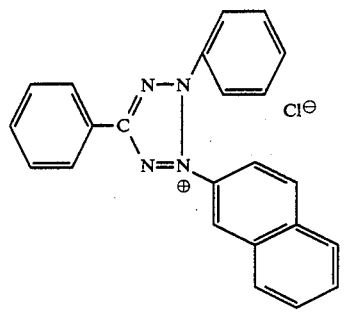

3-naphthyl-2,5-diphenyl-2H-tetrazolium chloride (TV)

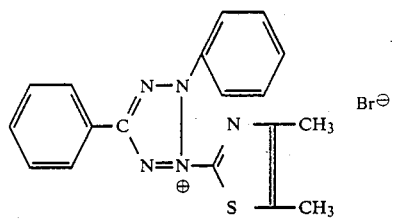

3-(4,5-dimethyl-2-thiazolyl)-2,5-diphenyl-2H-tetrazolium bromide (MTT)

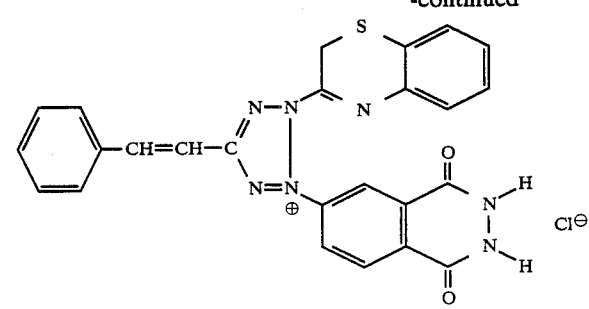

2-(2-benzthiazolyl)-3-(4-phthalylhydrazidyl)-5-styryl-2H-tetrazolium bromide (BPST)

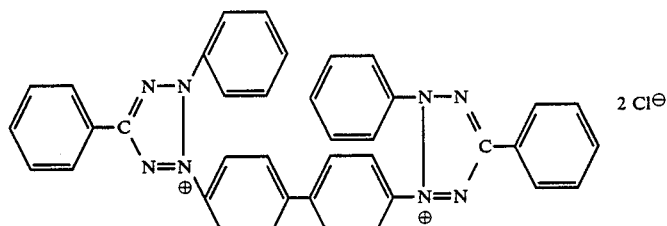

3,3'-(4,4'-biphenylene)-bis-(2,5-diphenyl-2H-tetrazolium chloride (NT)

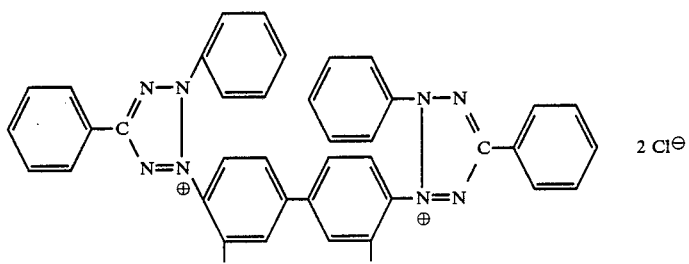

3,3'-(3,3'-dimethoxy-4,4'-biphenylene)-bis-(2,5-diphenyl-2H-tetrazolium chloride (BT)

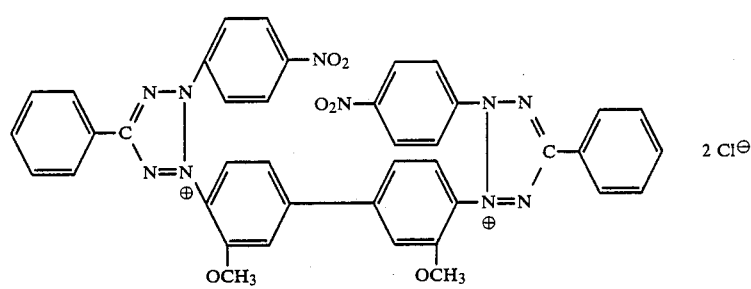

3,3'-(3,3'-dimethoxy-4,4'-biphenylene)-bis-(2-p-nitrophenyl-5-phenyl-2H-tetrazolium chloride (NBT)

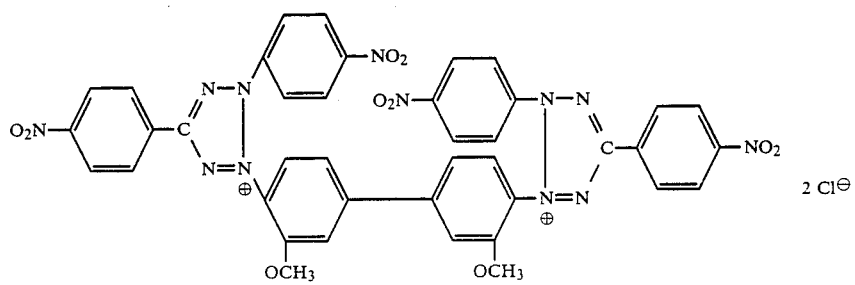

3,3'-(3,3'-dimethoxy-4,4'-biphenylene)-bis-(2,5-p-nitrophenyl-2H-tetrazolium chloride (TNBT)

as defined in Lehninger, Principles of Biochemistry, Warth Publishers, 1982, pp 470–475) of the resulting tetrazolium salt is 0 or lower volts. $R_3$–$R_5$ can be independently selected from phenyl, p-iodophenyl, p-nitrophenyl, naphthyl, thiazolyl, alkylthiazolyl, benzothiazolyl, phthalylhydrazidyl, styryl, biphenyl, 3-biphenylene-2,5 diphenyltetrazolium chloride, 3-dimethoxy 4-biphenylene 2,5-diphenyltetrazolium chloride, 3- dimethoxy-4-biphenylene 2-p-nitrophenyl-5-phenyltetrazolium chloride or 3-dimethoxy-4-biphenylene-2,5-p-nitrophenyltetrazolium chloride.

Tetrazolium salts are a group of heteroaromatic compounds. They are colorless or very slightly colored and freely soluble in water due to their ionic character. They form on reduction highly colored water insoluble compounds called formazans (i.e. groups of Formula IV). A number of tetrazolium salts are commercially available or are reported in the literature, which will form a colored precipitate when exposed to a leaving group described above. Representative tetrazolium salts include the following:

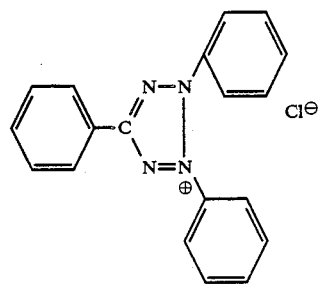

2,3,5-triphenyl-2H-tetrazolium chloride (TTC)

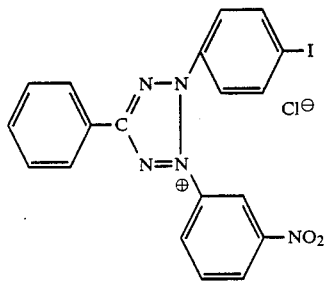

2-p-iodophenyl-3-p-nitrophenyl-5-phenyl-2H-tetrazolium chloride (INT)

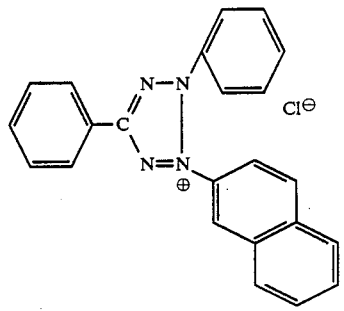

3-naphthyl-2,5-diphenyl-2H-tetrazolium chloride (TV)

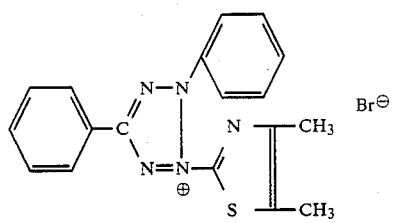

3-(4,5-dimethyl-2-thiazolyl)-2,5-diphenyl-2H-tetrazolium bromide (MTT)

-continued

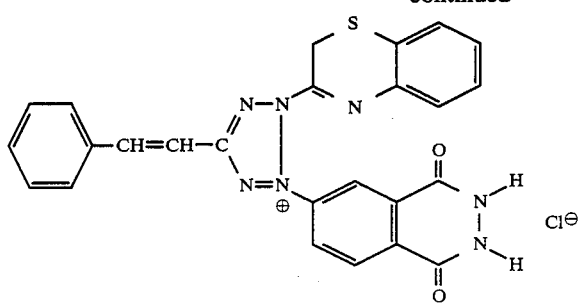

2-(2-benzthiazolyl)-3-(4-phthalylhydrazidyl)-5-styryl-2H-tetrazolium bromide (BPST)

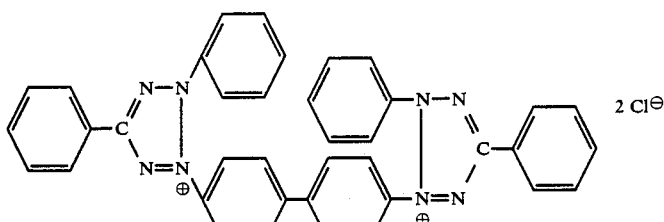

3,3'-(4,4'-biphenylene)-bis-(2,5-diphenyl-2H-tetrazolium chloride (NT)

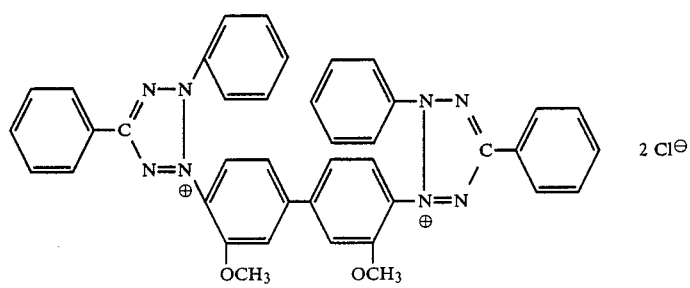

3,3'-(3,3'-dimethoxy-4,4'-biphenylene)-bis-(2,5-diphenyl-2H-tetrazolium chloride (BT)

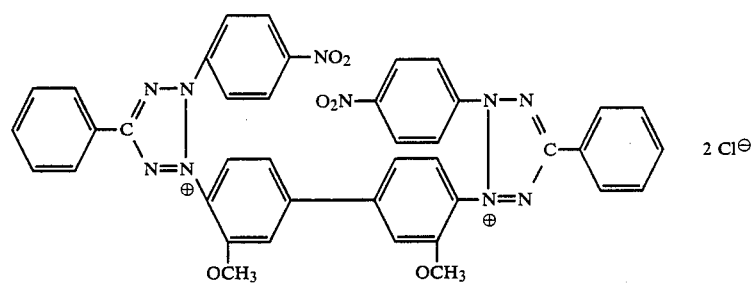

3,3'-(3,3'-dimethoxy-4,4'-biphenylene)-bis-(2-p-nitrophenyl-5-phenyl-2H-tetrazolium chloride (NBT)

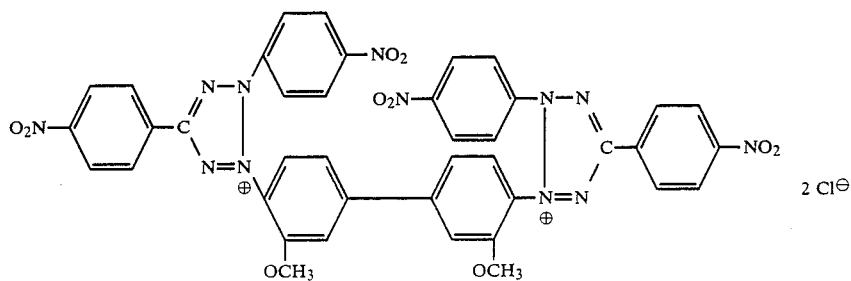

3,3'-(3,3'-dimethoxy-4,4'-biphenylene)-bis-(2,5-p-nitrophenyl-2H-tetrazolium chloride (TNBT)

The redox potentials ($E'_o$) of the tetrazolium salts shown above are provided below for various pH values.

| Tetrazolium | $E_o'$(volts) | pH |
|---|---|---|
| TNB$_T$ | −0.05 | 7.2 |

-continued

| Tetrazolium | $E_o'$(volts) | pH |
|---|---|---|
| NBT | −0.05 | 7.2 |
| INT | −0.09 | 7.2 |
| MTT | −0.11 | 7.2 |
| NT | −0.17 | 7.2 |
| NT | −0.22 | 7.6 |
| BT | −0.16 | 7.2 |
| BT | −0.23 | 7.6 |
| TT | −0.49 | 7.2 |
| TT | −0.37 | 7.6 |
| TT | −0.44 | 7.0 |

General Definitions

As used herein, the term "halo" or "halogen" refers to chloro, bromo, fluoro, and iodo groups, while the term "$C_1$ to $C_6$ alkyl" refers to lower alkyl groups including methyl, ethyl, propyl, isopropyl, butyl and the like.

"Conjugate Acid" is the protonated species of the leaving group anion.

Assay Methods and Kits

Assays can be performed using the cephalosporin derivatives and tetrazolium salts described above. In one such assay, the presence of β-lactamase producing bacteria can be detected by introducing into a sample of biological fluid suspected of containing such bacteria a compound of formula I and a compound of formula II. If β-lactamase producing bacteria are present, compound I will be cleaved, liberating a reducing group of formula III. The reducing group will reduce the tetrazolium salt of formula II to produce a colored formazan compound of formula IV.

Kits for assays for β-lactamase producing bacteria include compounds of formulae I and II either in the same or different solutions, or provided in dry form to be made into solution. The kit can include an appropriate buffer or dilution solution. In addition, an electron carrier (or accelerator) is desirable in the kit to introduce into the reaction mixture of the compounds of Formulae I and II. An accelerator is a molecular species which is transiently reduced by the leaving group, and then immediately reoxidized by release of electrons to the tetrazolium salt. The accelerator aids in the transfer of electrons from the leaving group to the tetrazolium salt. The use of an accelerator greatly increases the speed of the reaction. Preferred accelerators include phenazine methosulfate (PMS), phenazine ethosulfate, 1-alkoxy phenazinium methosulfate, and Meldola's Blue.

The reagents described above can also be used in assays where β-lactamase is used as a label for a specific binding member. "Specific binding member" means any substance or group of substances which has a specific binding affinity for a particular ligand and virtually none other. A "ligand" is the substance or group of substances the presence or amount of which is to be determined in the sample. For instance, the specific binding member can be an antibody, and the ligand can be the drug, protein or the like to be detected in the sample which binds to the antibody. Conversely, the specific binding member can be a drug, protein or the like which binds to the antibody to be detected in the sample. Other examples of specific binding member/ligand pairs include enzyme/enzyme receptors, carbohydrate/lectin, complementary nucleic acid strands, and the like.

The labelled specific binding member can be used in assays for ligand in a variety of different ways. The assay can be a heterogeneous or homogeneous assay, forward or reverse, or a liposome lytic immunoassay.

Assay kits for ligands employing reagents of this invention include β-lactamase conjugated to a specific binding member, a tetrazolium salt of formula II and a substrate of formula I. Appropriate buffer solutions and the like can also be included. In addition, an electron carrier (or accelerator) is desirable to aid in the transfer of electrons from the leaving group to the tetrazolium salt.

The examples which follow illustrate the invention, and are not intended to limit it. In Example 1, an assay employing a substrate of Formula I (7-thiophenylacetamido-3-thioacetoxymethyl-3-cephem-4-carboxylate sodium salt) is described. In Example 2, a β-hCG assay using a substrate of Formula I is described. In Example 3, another β-hCG assay is described. In Example 4, the sensitivity of the reagents of this invention is demonstrated. In Example 5, other assays for β-lactamase are described.

EXAMPLE 1

Assay for β-Lactamase Producing Bacteria

A. Synthesis of 7-Thiophenylacetamido-3-thioacetoxymethyl-3-cephem-4-carboxylate Sodium Salt

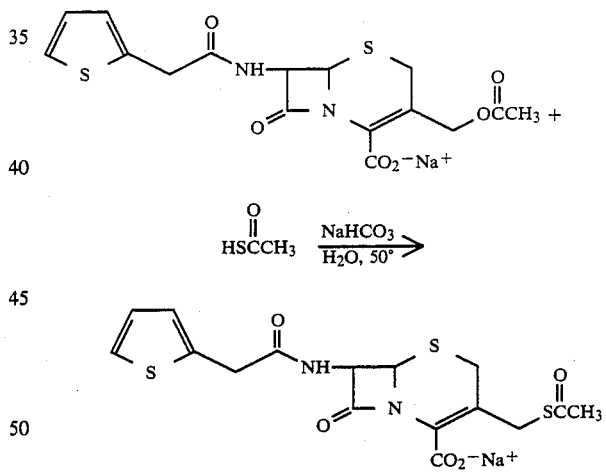

As illustrated in the reaction scheme above, thioacetic acid (0.776 g, 10.2 mmol) and sodium bicarbonate (0.857 g, 10.2 mmol) were dissolved in $H_2O$ (30 ml) and warmed to 50° C. The warm solution was filtered through silica gel, and added to a solution of cephalothin (1.43 g, 3.4 mmol) in $H_2O$ (10 ml). The reaction mixture was stirred for 31 hours at 50° C. After cooling to room temperature, the water was removed by vacuum, and the residue was dissolved in methyl alcohol. Crude product was precipitated by addition of diethyl ether, and the solid was triturated with ethyl acetate. Precipitation and trituration were repeated 7-thiophenylacetamido-3-thioacetoxymethyl-3-cephem-4-carbo xylate sodium salt (1.16 g) was obtained.

mp 207–210 dec.

IR (KBr, cm$^{-1}$) 3290, 1750, 1650, 1600, 1530, 1400, 1355.

NMR (D$_2$O,$\delta$): 2.30(3H,s); 3.45(2H,dd); 3.85(2H,dd); 3.90(2H,s); 5.05(1H,d); 5.60(1H,d); 7.00(2H,d); 7.30(1H,t).

B. Assay for $\beta$-Lactamase

Whatman #1 filter paper disks were impregnated with 0.05M phosphate buffer pH 7.0 and dried. The disks were saturated with a solution of $1 \times 10^{-3}$M INT, $2.5 \times 10^{-5}$M PMS, and $2.5 \times 10^{-3}$M the cephalosporin substrate of Part A in deionized water. The disks were dried at room temperature in the dark under high vacuum. Strips cut from these disks were then dipped in varying concentrations of $\beta$-lactamase from Enterobacter cloacae. A visible color change was observed with the strips turning reddish-pink. The greatest color change was observed with $1 \times 10^{-5}$M $\beta$-lactamase ($5 \times 10^{-10}$ moles deposited on the strip) with the limit of detectability at $1 \times 10^{-8}$M ($5 \times 10^{-13}$ moles deposited on the strip).

C. Control Experiment

As a control, solutions were prepared as described in part B above without $\beta$-lactamase, and analyzed as described above. No color change was observed with strips dipped in deionized water without enzyme.

EXAMPLE 2

$\beta$-hCG Assay Using $\beta$-lactamase/anti $\beta$-hCG IgG conjugate

A. Production of Anti $\beta$-hCG IgG

Antibody to $\beta$-hCG was produced by inoculating goats with the purified $\beta$ subunit of hCG combined with an adjuvant. This emulsion was then injected subcutaneously in the axillary and inguinal regions. A second injection was given 30 days later, and a third injection given 30 days after that. Two weeks later, a blood sample was drawn, and the serum tested for the presence of anti $\beta$-hCG IgG. When the antibody titer reached an acceptable level, the goat was put on a production bleeding schedule to harvest large volumes of serum. This serum was then accumulated and pooled for purification.

The purification was accomplished by passing the serum over a $\beta$-subunit specific affinity column. $\beta$-specific IgG was then collected, protein concentration calculated, and the antibody diluted to 3.5 mg/ml.

B. $\beta$-lactamase/Anti $\beta$-hCG IgG Conjugation with SMCC $\beta$-lactamase (P-99 from Porton Products) was conjugated to anti $\beta$-hCG IgG (Example 2, part A) using succinimidyl 4-(N-maleimidomethyl)cyclohexane 1-carboxylate (SMCC) from Pierce. Reduction of the antibody to generate thiols was accomplished by incubation of antibody (2 mg) at 3.5 mg/ml in 25 mM dithiothreitol (DTT) for 30 minutes at room temperature while rotating the mixture at 100 RPM. The DTT was then removed by passing the reduced antibody over a gel filtration (Sephadex G-25) column, collecting and pooling the antibody containing fractions.

$\beta$-lactamase (2 mg) at 2.0 mg/ml was modified by incubation with a 50 molar excess of SMCC in N,N-dimethylformamide (DMF) for 30 minutes at room temperature while rotating the mixture at 100 RPM. The unreacted reactants were then removed by passing the derivatized enzyme over a gel-filtration (Sephadex G-25) column, collecting and pooling the enzyme containing fractions.

The reduced antibody and modified enzyme were then combined at a molar ratio of 2.5 enzyme:1 antibody, and incubated 18 hours at 5° C. while rotating the mixture at 100 RPM. Unreacted thiols were then capped to block any further conjugation/aggregation by the addition of 100 ul of 5 mM N-ethylmaleimide to 1.5 ml of conjugate. Conjugates were then stored at 5° C. until utilized.

C. Preparation of Beads With Affinity Purified Goat Anti-$\beta$-hCG

5/16" polystyrene beads (from Evco) were ground to produce a rough surface. Affinity purified goat anti $\beta$-hCG (Example 2, part A) was adsorbed to the surface of the beads and the beads overcoated with a gelatin-sucrose mixture to block nonspecific binding.

D. Assay for $\beta$-hCG

A standard curve (FIG. 1) for $\beta$-hCG was generated using $\beta$-lactamase/anti $\beta$-hCG IgG conjugate of Example 2, Part B. This assay was performed in a heterogeneous bead format and used thiol-substituted cephalosporin (TAC) from Example 1 part A as the substrate.

One of the beads from part C was added to each well of a reaction tray containing 300 ul of $\beta$-hCG standards of known concentration. The beads were incubated with the standards for one hour at room temperature while the reaction tray was rotated at 180 RPM. The beads were washed with 3 pulses of 5 ml each of phosphate buffer to wash away unbound analyte. $\beta$-lactamase/anti $\beta$-hCG IgG conjugate (300 ul 4.0 ug/ml) of Example 2 part B was added to each well of the reaction tray. The beads were incubated with the conjugate for one hour at room temperature while the reaction tray was rotated at 180 RPM. The beads were then washed with 3 pulses of 5 ml each of phosphate buffer to wash away unbound conjugate. The beads were transferred to clean reaction tubes to which substrate mixture (1.0 ml) was added. The substrate mixture of $1.3 \times 10^{-3}$M iodonitrotetrazolium violet (INT), $3.2 \times 10^{-3}$M TAC, and $3.2 \times 10^{-5}$M phenazine methosulfate (PMS) in 0.1M NaPO$_4$, 0.1M NaCl, 0.32% BSA pH 7.0 was prepared. The beads were incubated with substrate mixture for one hour at room temperature while the reaction tubes were rotated at 180 RPM. The substrate mixture was then transferred to a clean cuvette, and the absorbance at 500 nm was read in a UV/Vis spectrophotometer. A$_{500}$ readings were then plotted against the standard concentrations to generate the standard curve of FIG 1.

Example 3

Assay for $\beta$-hCG Using $\beta$-lactamase/Anti $\beta$-hCG IgG Conjugates With 30-atom Linker

A. Preparation of $\beta$-lactamase/Anti $\beta$-hCG IgG Conjugate With 30-atom Linker $\beta$-lactamase (P-99 from Porton Products) was conjugated to anti $\beta$-hCG IgG (Example 2, part A) using succinimidyl 4-(N-maleimidomethyl) cyclohexyl tricaproamido-1-carboxylate (a 30 atom linker group) disclosed in U.S. patent application Ser. No. 114,930 filed Oct. 30, 1987 which was incorporated herein by reference. Reduction of the antibody to generate thiols was accomplished by incubation of antibody (2 mg) at 3.5 mg/ml in 25 mM dithiothreitol (DTT) for 30 minutes at room temperature while rotating the mixture at 100 RPM. The DTT was then removed by passing the reduced antibody over a gel filtration (Sephadex G-25) column, and the antibody-containing fractions were collected and pooled.

β-lactamase (2 mg) at 2.0 mg/ml was modified by incubation with a 50 molar excess of 30-atom linker arm in N,N-dimethylformamide (DMF) for 30 minutes at room temperature while the mixture was rotated at 100 RPM. The unreacted linker was then removed by passing the derivatized enzyme over a gel-filtration (Sephadex G-25) column, and the enzyme-containing fractions were collected and pooled.

The reduced antibody and modified enzyme were then combined at a molar ratio of 2.5 enzyme:1 antibody, and incubated 18 hours at 5° C. while the mixture was rotated at 100 RPM. Unreacted thiols were then capped to block any further conjugation/aggregation by the addition of 100 ul of 5 mM N-ethylmaleimide to 1.5 ml of conjugate. Conjugates were then stored at 5° C. until utilized.

B. Assay for β-hCG Using β-lactamase/Anti β-hCG IgG Conjugate With 30-atom Linker The assay of example 2 can be repeated using the conjugate of Example 3, part A instead of the conjugate of Example 2, part B.

EXAMPLE 4

UV/Vis Spectrophotometric Assay

In each of several cuvettes, 1) an aliquot (2.0 ml) of a solution containing $2 \times 10^{-3}$M INT, 0.05M phosphate buffer, and 1% bovine serum albumin pH 7.0, 2) $1 \times 10^{-2}$M thiol-substituted cephalosporin (TAC) from Example 1, part A in deionized water (1.0 ml), and 3) $1 \times 10^{-3}$M phenazine methosulfate (PMS) in deionized water (0.1 ml) were combined. To each cuvette, a β-lactamase solution (0.1 ml) at a concentration ranging from $5 \times 10^{-5}$M to $1 \times 10^{-7}$M in deionized water was added. The absorbance of the reaction mixture in each cuvette was monitored at 500 nm during a 90 minute period. The results were then compared to the absorbance of a control reaction mixture having the same concentrations of INT, TAC and PMS, but without enzyme. Sensitivity down to $1 \times 1^{-10}$ moles of β-lactamase was observed for this system.

EXAMPLE 5

Other Assays for β-Lactamase

A. General

Other assays were performed for β-lactamase using not only the tetrazolium salt and the substrate of Example 1, but other tetrazolium salts and substrates. The synthesis of the other substrates is described in parts C through G of this example. The assay method is described in part B cf this example, and the data obtained are reported in Table I.

B. Assay Method

An assay was performed by combining in a reaction vessel a solution of a tetrazolium salt, a β-lactamase substrate, and β-lactamase with or without an accelerator and bovine serum albumin (BSA) as indicated in Table I. During a period of time in which the reaction takes place (i.e. the "run time" indicated in Table I), the absorbance of the reaction mixture was monitored at the wavelength indicated in the column captioned "wavelength". The maximum absorbance was recorded for each mixture tested. For each mixture, a control solution was prepared which was identical to the reaction mixture, except that no β-lactamase was added. The absorbance of the control was recorded in each case at 500 nm, and the ratio of the maximum absorbance to the control solution absorbance was recorded (last column in Table I captioned "Ratio"). A ratio greater than 1.0 indicated an observable reaction in the reaction mixture in the "run time". Unless indicted by an asterisk (*), the β-lactamase the experiments indicated by the asterisk (*), β-lactamase from Porton Products (P-99) was used.

C. Synthesis of 7-Thiophenylacetamido-3-(4-bromothiophenoxy)methyl-3-cephem-4-carboxylate Sodium Salt

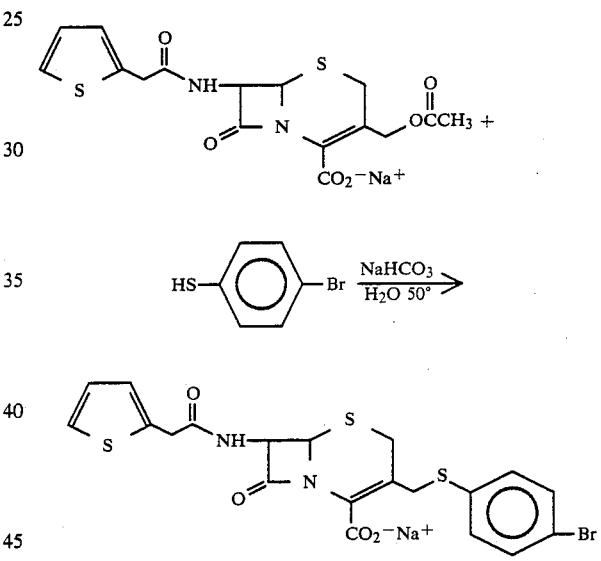

As shown in the reaction scheme above, 4-bromothiophenol (1.285 g, 6.8 mmol) and sodium bicarbonate (0.571 g, 6.8 mmol) were stirred in water (20 ml) and heated to 50° C. The mixture was filtered through silica gel, and the filtrate was added to cephalothin (0.948 g, 2.27 mmol) in water (5 ml). The mixture was stirred for 30 hours at 50° C. The solvent was removed under vacuum. The residue was dissolved in methanol, and diethyl ether was added to precipitate pure 7-thiophenylacetamido-3-(4-bromothiophenoxy)methyl-3-cephem-4-carboxylate sodium salt.

mp 163–171 dec.

IR (KBr, cm$^{-1}$) 3420, 1750, 1650, 1600, 1400, 1090, 1010, 810, 700.

NMR (DMSO-d$_6$, δ): 3.35(2H,dd); 3.72(2H,s); 4.22(2H,dd); 4.75(1H,d); 5.40(1H,dd); 6 85(2H,t); 7.35(5H,m); 8.93(1H,d).

D. Synthesis of 7-Thiophenylacetamido-3-(3-hydroxy-2-thiopyridyl)-methyl-3-cephem-4-carboxylate Sodium Salt

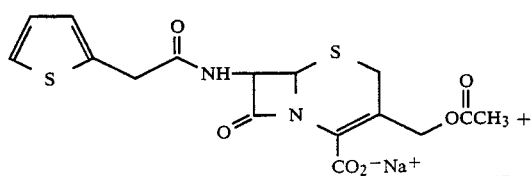

hydroxy-2-thiopyridyl) methyl 3 cephem-4-carboxylate sodium salt (0.677 g).

mp 175–184 dec.

IR (KBr, cm$^{-1}$) 3260, 1740, 1550, 1350, 690.

NMR (DMSO-d$_6$, δ): 3.72(2H,dd); 3.76(2H,s); 4.40(2H,s); 5.28(1H,dd); 5.50(1H,d); 6.58(1H,d); 6.90–7.03(3H,m); 7.30(1H,d); 7.38(1H,d); 9.18(1H,d).

E. Synthesis of 7-Thiophenylacetamido-3-thiobenzoyl methyl-3-cechem-4-carboxylate Sodium Salt

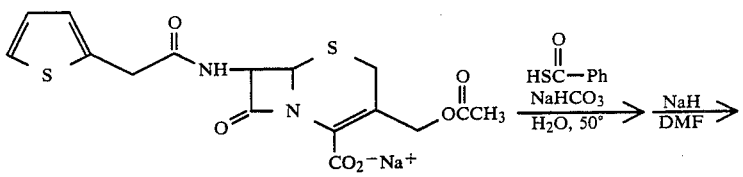

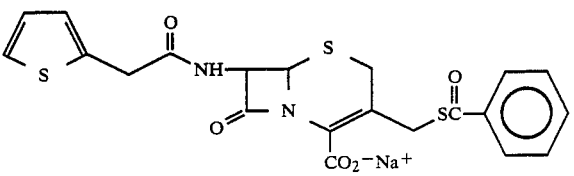

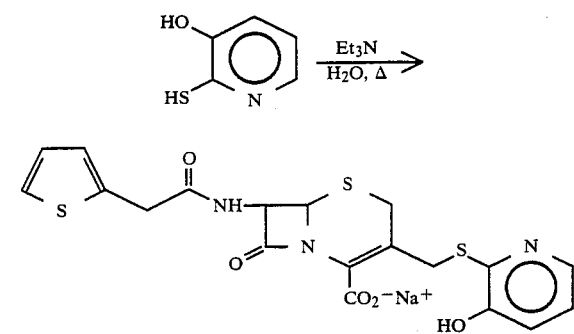

As illustrated in the reaction scneme above, cephalothin (1.06 g, 2.5 mmol) was added to a solution of 2-mercapto-3-pyridinol (0.322 g, 2 5 mmol) and triethylamine (0.257 g, 2.5 mmol) in H$_2$O (50 ml). The mixture was stirred for six hours at 70° C. The water was removed under reduced pressure. The residue was dissolved in 1:1 MeOH/benzene, and product was precipitated by addition of diethylether. Two further repetitions of this procedure yielded pure 7-thiophenylacetamido-3-(3-

Thiobenzoic acid (1.41 g, 10.2 mmol) and sodium bicarbonate (0.857 g, 10.2 mmol) were stirred in 30 ml of H$_2$O and heated to 50° C. The mixture was filtered through silica gel, and the filtrate was added to cephalothin (1.43 g, 3.4 mmol) in 20 ml of H$_2$O. The reaction mixture was stirred for 20 hours at 50° C. 7-Thiophenylacetamido-3-thiobenzoylmethyl-3-cephem-4-carboxylic acid (0.791 g) was collected by filtration. 50 mg of this material was dissolved in DMF (2 ml). Sodium hydride (4.4 mg. 0.11 mmol) was added, and the mixture was stirred for two hours, filtered, and dried under vacuum. The residue was dissolved in water, refiltered and lyophilized to yield pure 7-thiophenylacetamido-3-thiobenzoylmethyl-3-cephem-4-carboxylate sodium salt.

mp 239–241 dec.

IR (KBr, cm$^{-1}$) 3400, 3280, 1736, 1588, 1526, 1345, 1185, 910, 685.

NMR (DMSO-d$_6$, δ): 3.35(2H,dd); 3.78(2H,s); 4.25(2H,dd); 4.96(1H,d); 5.47(1H,dd); 6.95(2H,t); 7.35(1H,d); 7.58(2H,t); 7.71(1H,t); 7.96(2H,d); 9.04(1H,d).

F. Synthesis of 7-Thiophenylacetamido-3-(4-aminothiophenoxy)methyl-3-cephem-4-carboxylate Sodium Salt

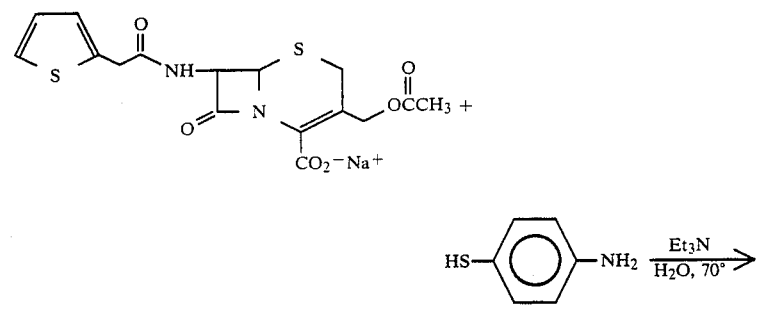

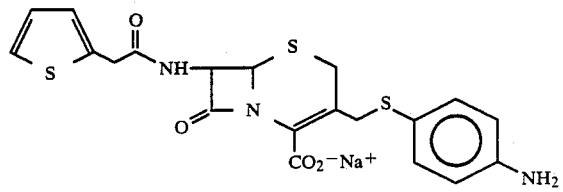

As illustrated in the reaction scheme above, 4-aminothiophenol (0.580 g, 4.6 mmol) was dissolved in DMF (10 ml). This solution was added to water (100 ml) containing triethylamine (4.6 mmol, 0.465 g). Cephalothin (1.94 g, 4.6 mmol) was added, and the mixture was brought to 70° C. and stirred for six hours. The mixture was cooled to room temperature, and the water was removed by vacuum. The residue was twice precipitated from 1:1 MeOH/benzene by addition of diethyl ether to yield pure 7-thiophenylacetamido-3-(4-aminothiophenoxy) methyl-3-cephem-4-carboxylate sodium salt (1.026 g).

mp 169–175.

IR (KBr, cm$^{-1}$) 3360, 3020, 1740, 1580, 1490, 1380, 1180.

NMR (DMF-d$_7$, δ): 3.33(2H,dd); 3.52(2H,s); 4.38(2H,dd); 4.93(1H,d), 5.62(1H,dd); 6.62(2H,d); 6.95(2H,t); 7.17(2H,d); 7.40(1H,d); 8.95(1H,dd).

G. Synthesis of 7-Thiophenylacetamindo-3-(S-cysteinvl)methyl-3-cephem-4-carboxylate Sodium Salt

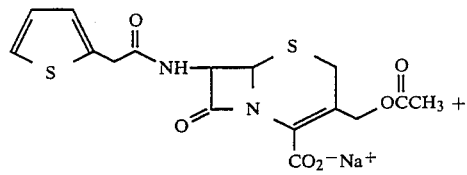

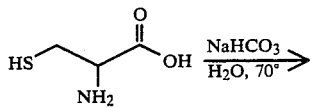

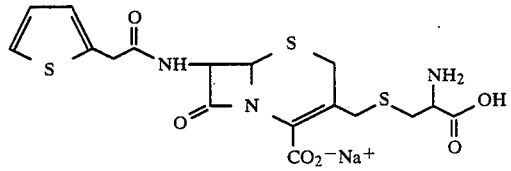

L-Cysteine (2.10 g, 17.3 mmol) and sodium bicarbonate (1.45 g, 17.3 mmol) were dissolved in water (50 ml) and heated to 70° C. The warm solution was filtered through silica gel into cephalothin (2.42 g, 5.77 mmol) in water (10 ml). The combined solution was stirred for 30 hours at 70° C. The solvent was removed under reduced pressure. The residue was dissolved in DMF, and 2-propanol was added to precipitate 7-thiophenylacetamido-3-(S-cysteinyl)methyl-3-cephem-4-carboxylate sodium salt.

EXAMPLE 6
Assay for Urinary Tract Infection

A. Preparation of Urinary Tract Infection Antibodies

Antibodies to urinary tract infectious microorganisms were raised by innoculating rabbits with emulsions containing heat inactivated microorganisms including *Pseudomonas auruginosa, Streptococcus D, Escherichia coli, Proteus mirabilis,* and *Klebsiella pneumoniae,* each rabbit being injected with a different microorganism. Rabbits were injected with the emulsions subcutaneously and intramuscularly, later injections were given 21 days later, and third injections were given 21 days after that. One week later, blood samples were drawn and the serum tested for the presence of antibodies to the antigen pool described above. When the antibody titer reached an acceptable level, each rabbit was put on a production bleeding schedule to harvest sufficient volumes of serum for purification of antibodies to a particular urinary tract infectious microorganism. The serum was purified by passing the serum through a DE52 (Whatman) anion exchange column to separate IgG from other proteins. The antibody containing fractions were then collected for each rabbit, and the protein concentration calculated. The antibodies against the various microorganisms were then pooled, and the antibody pool diluted to 1.1mg/ml.

B. Preparation of Microparticles With Antibacterial Antibody

The rabbit antibacterial IgG from part A above was coupled using EDC (1-ethyl-3-(3-dimethylamino-propyl) carbodiimide hydrochloride) to polystyrene carboxylated microparticles (Seradyn, Indianapolis, Ind.)

as described in Avrameas, S. C. R., Acad. Sci. Paris, Vol. 262, p. 2543 (1966).

C. Preparation of Enzyme/Antibody Conjugates

A β-lactamase/antibacterial IgG conjugate was produced following the procedure outlined in Example 2, part B, substituting the antibacterial IgG produced in part A of this example for the β-HCG IgG of Example 2, part B for use in an assay for urinary tract infectious microorganisms described in part D below.

D. Assay for Urinary Tract Infectious Microorganisms

The microparticles from part B of this example coupled to antibody were suspended in a buffer (phosphate-buffered saline from Sigma Chemical and 0.1% sodium azide, pH 7.4 to a concentration of 0.08%). The microparticles (135 ul; 0.08% solids) were combined with a sample (1.0 ml) containing $10^7$ urinary tract infectious microorganisms per milliliter and EDTA/Sarcosyl (Sigma Chemical) extraction buffer (135 microliters), and the mixture was incubated at room temperature for five minutes. The mixture was then poured through a porous filter media (a Testpack device sold by Abbott Laboratories, Abbott Park, Ill.), and washed with buffer (1.0 ml of 1.0 M guanidine-HCl, 1.0 M NaCl, 0.1% Tween 20, 0.1% sodium azide; hereinafter "buffer A"). The β-lactamase antibacterial IgG conjugate solution of part C of this example (200 ul; 100 micrograms/ml) was added to the filter media and incubated at room temperature for five minutes The filter media was then washed with buffer A (1 ml). A solution (200 microliters) containing INT ($2.4 \times 10^{-4}$ molar), TAC ($4.8 \times 10^{-3}$ molar), PMS ($4.8 \times 10^{-4}$ molar) and sodium phosphate (0.1 molar) pH 7.0 was then passed through the filter media and incubated at room temperature for five minutes. The filter media was then washed with buffer A (1.0 ml) and visually compared to a control filter media which was treated in the same fashion, but without the bacteria. The bacteria-containing filter media was pink compared to the control which remained white, indicating that bacteria was detected by the assay in the bacteria-containing filter media.

What is claimed is:

1. A method for detecting β-lactamases in a sample, comprising:
   (a) exposing said sample to a β-lactamase substrate of formula I:

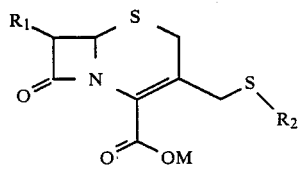

wherein $R_1$ is a group which maintains the ability of said substrate to be recognized as a substrate by β-lactamases and cleave the β-lactam ring; and
   $R_2$, together with the sulfur atom to which it is attached, form a leaving group which is released into solution, the conjugate acid of which has a pKa in water of less than 8, and M is hydrogen or a group I metal;
   (b) exposing said leaving group to a tetrazolium salt of formula II:

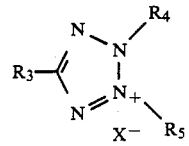

wherein $R_3$, $R_4$ and $R_5$ are independently selected from groups such that the redox potential of the resulting tetrazolium salt is 0 or lower volts; and
   X is an anion; whereby a colored precipitate is formed in the presence of the leaving group; and
   (c) monitoring said colored precipitate as an indicator of the presence of an active β-lactamase.

2. The method of claim 1 wherein said leaving group is selected from the group consisting of halo or amino substituted thiophenol; hydroxy, halo, or amino substituted mercapto pyridine; aliphatic or aromatic thiolcarboxylic acid; and mercapto amino acid.

3. The method of claim 2 wherein said leaving group is selected from the group consisting of p-bromo thiophenol, p-amino thiophenol, 2-mercapto-3 pyridinol, thiolacetic acid, thiobenzoic acid, and cysteine.

4. The method of claim 1 wherein $R_1$ is selected from the group consisting of amino,thiophene-2-acetamido, benzyl-2-acetamido, phenoxy 2-acetamido, D--aminoadipamido, 2-amino 2-phenylacetamido, tetrazolylacteamido, 4-pyridylthioacetamido, and a group of the formula:

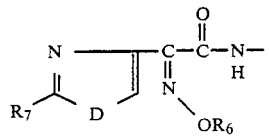

where $R_6$ is a lower aliphatic group, $R_7$ is an amino or alkylamino group, and D is an oxygen or sulfur atom.

5. The method of claim 4 wherein $R_1$ is selected from the group consisting of 2-(2-amino-4-thiazolyl)-2-(methoxyimino)acetamido-2-(2-amino-4-thiazolyl)-2-(carboxymethoxyimino)acetamido, and 2-(2-amino-4-thiazolyl)-2-(hydroxyimino) acetamido.

6. The method of claim 1 wherein $R_3$, $R_4$ and $R_5$ are independently selected from the group consisting of phenyl, p-iodophenyl, p-nitrophenyl, naphthyl, thiazolyl, alkylthiazolyl, benzothiazolyl, phthalylhydrazidyl, styryl, biphenyl, 3-biphenylene-2,5-diphenyltetrazolium chloride, 3-dimethoxy-4-biphenylene-2,5-diphenyltetrazolium chloride, 3-dimethoxy-4-biphenylene-p-nitrophenyl-5-phenyltetrazolium chloride and 3-dimethoxy-4-biphenylene-2,5-nitrophenyltetrazolium chloride.

7. An assay kit for detecting β-lactamase in a sample, comprising:
   (a) a β-lactamase substrate of formula I:

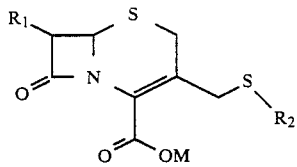

wherein R₁ is a group which maintains the ability of said substrate to be recognized as a substrate by β-lactamases and cleave the β-lactam ring; and R₂, together with the sulfur atom to which it is attached, form a leaving group which is released into solution, the conjugate acid of which has a pKa in water of less than 8, and M is hydrogen or a group I metal; and (b) a tetrazolium salt of Formula II:

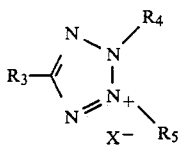

wherein R₃, R₄ and R₅ are independently selected from groups such that the redox potential of the resulting tetrazolium salt is 0 or lower volts; and X is an anion.

8. The assay kit of claim 7 further comprising an accelerator.

9. The assay kit of claim 8 wherein said accelerator comprises phenazine methosulfate.

10. The assay kit of claim 7 wherein said compounds of Formulae I and II are disposed on a solid phase.

11. The assay kit of claim 10 wherein said solid phase comprises a strip.

12. The assay kit of claim 7 wherein said leaving group is selected from the group consisting of an aliphatic or aromatic thiol; a halo or amino substituted thiophenol; hydroxy, halo, or amino substituted mercapto pyridines; aliphatic or aromatic thiolcarboxylic acids; a thiosulfonic acid; or a mercapto amino acid.

13. The assay kit of claim 7 wherein said leaving group is selected from the group consisting of p-bromo thiophenol; p-aminothiophenol, 2-mercapto-3-pyrridinol; thiolacetic acid; thiobenzoic acid; and cysteine.

14. The assay kit of claim 7 wherein R₁ is selected from the group consisting of amino, thiophene-2-acetamido, benzyl-2-acetamido, phenoxy-2-acetamido, D-2-aminoadipamido, 2-amino-2-phenylacetamido, tetrazolylacteamido, 4-pyridylthioacetamido, and a group of the formula:

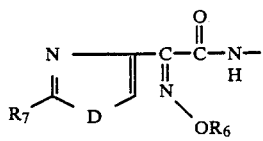

where R₆ is a lower aliphatic group, R₇ is an amino or alkylamino group, and D is an oxygen or sulfur atom.

15. The assay kit of claim 14 wherein R₁ is selected from the group consisting of 2-(2-amino-4-thiazolyl)-2-(methoxyimino)acetamido.2-(2-amin o-4-thiazolyl) 2-(carboxymethoxyimino)acetamido, and 2-(2-amino-4-thiazolyl)-2-(hydroxyimino)acetamido.

16. The assay kit of claim 7 wherein R₃, R₄ and R₅ are independently selected from the group of phenyl, p-iodophenyl, p-nitrophenyl, naphthyl, thiazolyl, alkylthiazolyl, benzothiazolyl, phthalylhydrazidyl, styryl, biphenyl, 3-biphenylene-2,5-diphenyltetrazolium chloride, 3-dimethoxy-4-biphenylene 2,5-diphenyltetrazolium chloride, 3-dimethoxy-4-biphenylene 2-p-nitrophenyl-5-phenyltetrazolium chloride and 3-dimethoxy-4-biphenylene-2,5-p-nitrophenyltetrazolium chloride.

17. An assay kit for the detection of ligand in a sample, comprising:

(a) a conjugate of a specific binding member to the ligand and a β-lactamase substrate of formula I:

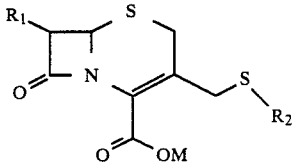

wherein R₁ is a group which maintains the ability of said substrate to be recognized as a substrate by β-lactamases and cleave the β-lactam ring; and R₂, together with the sulfur atom to which it is attached, form a leading group which is released into solution, the conjugate acid of which has a pKa in water of less than 8, and M is hydrogen or a group I metal; and (b) a tetrazolium salt of formula II:

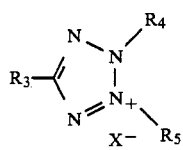

wherein R₃, R₄ and R₅ are independently selected selected from groups such that the redox potential of the resulting tetrazolium salt is 0 or lower volts; and X is an anion.

18. The assay kit of claim 17 further comprising an accelerator.

19. The assay kit of claim 18 wherein said accelerator comprises phenazine methosulfate.

20. The assay kit of claim 17 wherein said group is selected from the group consisting of an aliphatic or aromatic thiol; a halo or amino substituted thiophenol; hydroxy, halo, or amino substituted mercapto pyridines; aliphatic or aromatic thiolcarboxylic acids; a thiosulfonic acid; and a mercapto amino acid.

21. The assay kit of claim 17 wherein said group is selected from the group consisting of 4-bromothiophenol; 4-aminothiophenol, 2-mercapto 3 pyridinol; thiolacetic acid; thiobenzoic acid; or 22. The assay kit of claim 17 wherein R₁ is selected from the group consisting of amino, thiophene-2-acetamido, benzyl-2-acetamido, phenoxy-2-acetamido, D-2-aminoadipamido, 2-amino-2-phenylacetamido, tetrazolylacetamido, 4-pyridylthioacetamido, 2-(2-amino-4-thiazolyl)-2-(methoxyimino)acetamido-2-(2-amino-4-thiazolyl)-2-(carboxymethoxyimino)acetamido, and 2-(2-amino-4-thiazolyl)-2-(hydroxyimino)acetamido.

23. The assay kit of claim 17 wherein R₃, R₄ and R₅ are independently selected from the group consisting of phenyl, p-iodophenyl, p-nitrophenyl, naphthyl, thiazolyl, alkylthiazolyl, benzothiazolyl, phthalylhydrazidyl, styryl, biphenyl, 3-biphenylene-2,5 diphenyltetrazolium chloride, 3-dimethoxy-4-biphenylene-2,5-diphenyltetrazolium chloride, 3-dimethoxy-4-biphenylene-2-p-nitrophenyl-5-phenyltetrazolium chloride and 3-dimethoxy-4-biphenylene-2,5-p-nitrophenyltetrazolium chloride.

* * * * *

UNITED STATES PATENT AND TRADEMARK OFFICE
CERTIFICATE OF CORRECTION

PATENT NO. : 4,978,613

DATED : December 18, 1990

INVENTOR(S) : Christopher Bieniarz, et al.

It is certified that error appears in the above-identified patent and that said Letters Patent is hereby corrected as shown below:

On the title page:

The title page should be deleted to appear, as per attached title page.

The sheet of Drawing consisting of figure 1 should be added as shown on the attached sheet.

Columns 1 through 26, should be deleted to be replaced with columns 1 through 26 as per attached.

Signed and Sealed this

Thirty-first Day of March, 1992

Attest:

HARRY F. MANBECK, JR.

Attesting Officer      Commissioner of Patents and Trademarks

United States Patent [19]

Bieniarz et al.

[11] Patent Number: 4,978,613

[45] Date of Patent: Dec. 18, 1990

[54] BETA-LACTAMASE ASSAY EMPLOYING CHROMOGENIC PRECIPITATING SUBSTRATES

[75] Inventors: Christopher Bieniarz, Highland Park; Michael J. Cornwell; Douglas F. Young, both of Lake Villa, all of Ill.

[73] Assignee: Abbott Laboratories, Abbott Park, Ill.

[21] Appl. No.: 298,098

[22] Filed: Jan. 17, 1989

[51] Int. Cl.$^5$ ............................................... C12Q 1/34
[52] U.S. Cl. ............................................ 435/18; 435/4
[58] Field of Search ........................................... 435/18

[56] References Cited

PUBLICATIONS

Dojin–Chem. Abst., vol. 101 (1984), p. 186950s.
Tanaka et al.–Chem. Abst., vol. 104 (1986), p. 203469y.
Osokina et al.–Chem. Abst., vol. 105 (1986), p. 111915h.
Wielinger et al.–Chem. Abst., vol. 99 (1983), p. 152,073h.

*Primary Examiner*—Sam Rosen
*Attorney, Agent, or Firm*—James D. McNeil; Priscilla E. Porembski

[57] ABSTRACT

A method for detecting $\beta$-lactamases which may be present in a sample by using a disclosed chromogenic precipitating substrate. A sample is exposed to a disclosed $\beta$-lactamase substrate and a colored precipitate forms in the presence of an active $\beta$-lactamase.

23 Claims, 1 Drawing Sheet

BETA-LACTAMASE ASSAY EMPLOYING CHROMOGENIC PRECIPITATING SUBSTRATES

BACKGROUND OF THE INVENTION

1. Technical Field

This invention relates to assays employing chromogenic reactions in which one of the reagents is a cephalosporin substrate of β-lactamase.

2. Description of Related Art

β-lactamases are enzymes produced by certain bacteria. These enzymes confer on these bacteria resistance to β-lactam antibiotic therapy. The capacity to produce β-lactamase is probably the most important and common cause of resistance to β-lactam antibiotics in bacteria. For instance, if a patient infected with bacteria producing β-lactamase is treated with cephalosporin, many β-lactamases will recognize the cephalosporin and convert it into a metabolite with little or no antibiotic potency. Screening patient samples for β-lactamase activity can avoid subjecting the patient to a course of therapy with inappropriate antibiotics.

β-lactamases also have uses as a label in enzyme immunoassays (EIAs). β-lactamases have very high turnover numbers, are easily available in high purity from many commercial sources, have pH optima compatible with ligand-antibody binding, are relatively stable, have low molecular weight, are inexpensive, and are usually absent in body fluids.

By contrast, other commonly used enzyme labels such as alkaline phosphatase, horseradish peroxidase, and β-galactosidase do not have all of these advantages in common. For instance, horseradish peroxidase requires chromogenic substrates unstable to varying degrees in the presence of hydrogen peroxide, and immunogenicity and mutagenicity of the chromogenic substrates for horseradish peroxidase are potential problems. Another disadvantage is the low yield of the horseradish peroxidase/IgG conjugation and loss of enzyme activity after conjugation. Furthermore, horseradish peroxidase exhibits markedly different stability characteristics at different pH values. Horseradish peroxidase is, also difficult to use because of hemolysis problems and cross-reactivity of its substrates with hemoglobin.

β-galactosidase substrates are often subjected to high rates of non-enzymatic hydrolysis leading to high numbers of failed tests. In addition, a loss of enzymatic activity upon enzyme conjugation can occur. Finally, the high molecular weight of β-galactosidase presents problems in some applications. As a result, few if any commercial products exist utilizing β-galactosidase.

Alkaline phosphatase is a readily available enzyme at reasonable cost. However, the efficiency of conjugation of alkaline phosphatase is rather low, typically about 5 percent, and after conjugation, only about 10 percent or less of the immunological activity of the ligand conjugated to alkaline phosphatase remains. Thermal stability of the conjugates of alkaline phosphotase is typically very low. Furthermore, because many samples from humans contain alkaline phosphatase, it is difficult to detect the labelled alkaline phosphatase from the endogenous alkaline phosphatase activity.

SUMMARY OF THE INVENTION

The present invention is a method and kit for the detection of β-lactamase enzymes in samples containing noassays which use β-lactamase as a label. The method of the present invention includes detecting β-lactamase activity in a sample by exposing the sample to a β-lactamase substrate of formula I

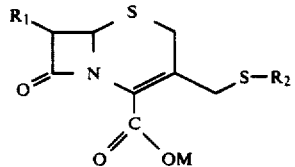

$R_1$ is a group which maintains the ability of the cephalosporin substrate I to be recognized by β-lactamase. When the compound is exposed to a β-lactamase, the $R_2$ group, together with the sulfur atom to which it is attached, form a leaving group the conjugate acid of which has a pKa in water of less than 8. M is hydrogen or a group I metal. After the β-lactamase-containing sample is exposed to a compound of formula I and the leaving group is generated, the leaving group is exposed to a tetrazolium salt of formula II

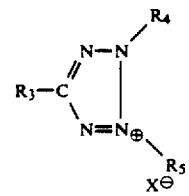

wherein $R_3$, $R_4$ and $R_5$ are independently selected from groups such that the redox potential of the resulting tetrazolium salt is 0 or lower volts. X is an anion.

When the leaving group of substrate I is exposed to the tetrazolium salt, a colored precipitate of formazan is formed in the presence of the leaving group which indicates that the sample contains a β-lactamase enzyme.

The current invention also involves kits for the detection of β-lactamase in samples and assays which employ β-lactamase as labels.

BRIEF DESCRIPTION OF THE DRAWING

FIG. 1 is a standard curve obtained when using reagents of this invention in an assay for β-hCG.

DETAILED DESCRIPTION OF THE INVENTION

General

This invention involves kits and methods for the detection of β-lactamases. Preferred enzymes detected by the claimed method and kit are a subclass of β-lactamases designated as cephalosporinases. The claimed kits and method involve exposing the enzyme to cephalosporins of formula I in the presence of the tetrazolium salt of formula II as illustrated in the reaction scheme

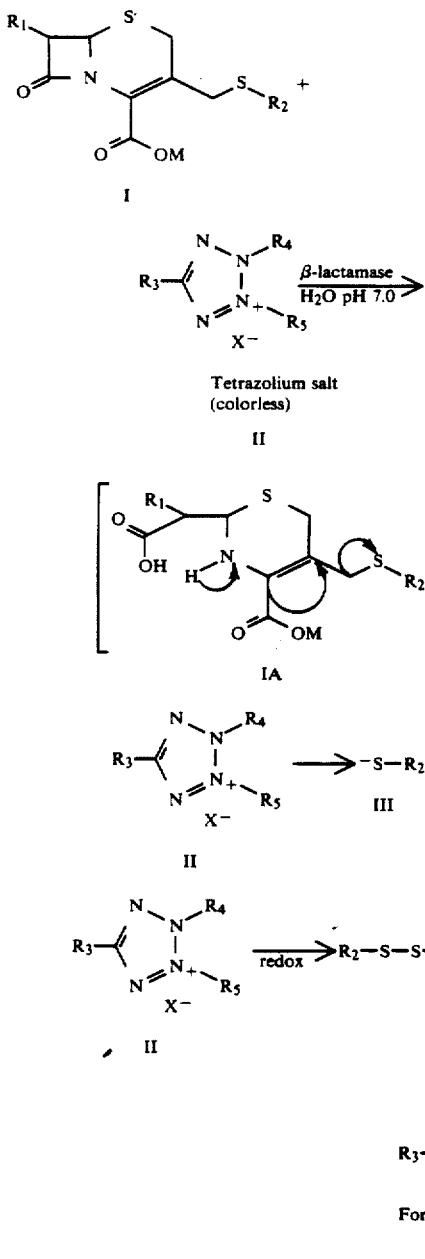

by an acetamide group. Appropriate substituents for the groups above include halogen, cyano, sulfoxy or sulfonyl group(s).

$R_1$ can also be an amino, substituted or unsubstituted alkylamino, substituted or unsubstituted arylamino group, or substituted or unsubstituted aromatic or non-aromatic heterocyclic substituted amino group. Alkylamino or arylamino groups can be substituted with either an aliphatic straight or branched chain or an alicyclic group.

$R_1$ can also be a group of the formula:

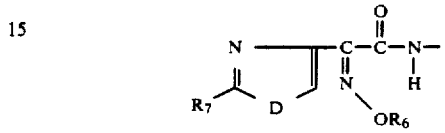

where $R_6$ is a lower aliphatic group, and $R_7$ is an amino or alkylamino group, and D represents an oxygen or sulfur atom. $R_1$ can also be a group of the formula:

where $R_8$ is a 4–6 membered heterocyclic ring.

Preferred groups for $R_1$ include those of the formulae:

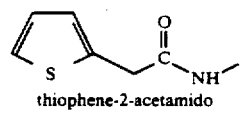
thiophene-2-acetamido

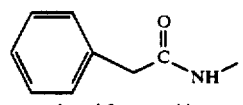
phenyl-2-acetamido

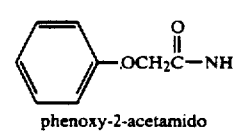
phenoxy-2-acetamido

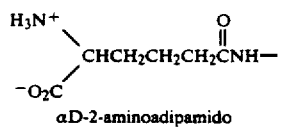
αD-2-aminoadipamido

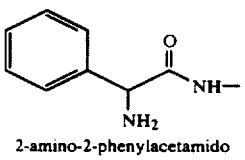
2-amino-2-phenylacetamido

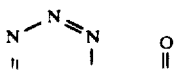

The β-lactamase cleaves the lactam ring in substrate I to create an intermediate compound IA which produces a leaving group of formula III. The leaving group reacts with the tetrazolium salt of formula II to produce a colored precipitate of formazan (Formula IV), indicating the presence or quantity of β-lactamase.

$R_1$ Definition $R_1$, as indicated above, is a group which maintains the ability of the substrate of formula I to be recognized as a substrate by β-lactamases and cleave the β-lactam ring. $R_1$ can be a substituted or unsubstituted phenyl group linked to the lactam ring by an acetamide group, a substituted or unsubstituted alicyclic hydrocarbon

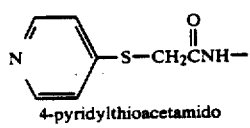

4-pyridylthioacetamido

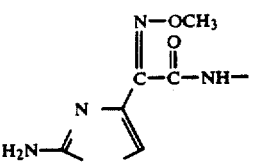

2-(2-amino-4-thiazolyl)-2-(methoxyimino)acetamido

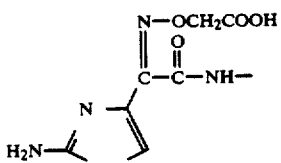

2-(2-amino-4-thiazolyl)-2-(carboxymethoxyimino)acetamido

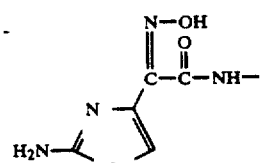

2-(2-amino-4-thiazolyl)-2-(hydroxyimino)acetamido $R_1$ also includes alkoxycarbonyl, halogen, cyano, sulfoxy, or aminosulfonyl.

This is only a representative list of the possible $R_1$ substituents. With reasonable experimentation, those of ordinary skill will find other $R_1$ substituents which will preserve the ability of the compound of formula I to serve as a substrate for $\beta$-lactamase for cephalosporins.

$R_2$ Definition

As indicated above, $R_2$ forms a leaving group with the sulfur atom to which it is attached. As a consequence of the $\beta$-lactamase catalyzed $\beta$-lactam ring cleavage, the leaving group is released into solution. The conjugate acid of the leaving group must have a pKa of less than about ten such that the tetrazolium salt of formula II can be reduced to produce a colored precipitate of formazan of Formula IV above. The reduction of tetrazolium salts to colored formazans by the leaving group is pH dependent, and is facilitated by the increase of pH of the solution. Thus since the reductions are carried at pH 6.0–9.0, preferably pH 7.0, the best leaving groups are those significantly deprotonated in the aforesaid pH range, e.g., thiols having pKa 8 or lower. Naturally this requirement will suggest a wide variety of leaving groups to those of ordinary skill in the art which can be ascertained with reasonable experimentation. Preferred leaving groups include an aliphatic or aromatic thiol; halo or amino substituted thiophenol; hydroxy, halo, or amino substituted mercapto pyridines; aliphatic or aromatic thiol acids; thiosulfonic acids; or a mercapto amino acid. Such preferred leaving groups include p-bromo-thiophenol, p-amino-thiophenol, 2-mercapto-3 pyridinol, thiolacetic acid, thiobenzoic acid, or cysteine.

$R_3$–$R_5$ Definition $R_3$–$R_5$ are independently selected from groups such that the redox potential ($E'_o$, as defined in Lehninger, Principles of Biochemistry, Warth Publishers, 1982, pp 470–475) of the resulting tetrazolium salt is 0 or lower volts. $R_3$–$R_5$ can be independently selected from phenyl, p-iodophenyl, p-nitrophenyl, naphthyl, thiazolyl, alkylthiazolyl, benzothiazolyl, phthalylhydrazidyl, styryl, biphenyl, 3-biphenylene-2,5 diphenyltetrazolium chloride, 3-dimethoxy-4-biphenylene 2,5-diphenyltetrazolium chloride, 3-dimethoxy-4-biphenylene-2-p-nitrophenyl-5-phenyltetrazolium chloride or 3-dimethoxy-4-biphenylene-2,5-p-nitrophenyltetrazolium chloride.

Tetrazolium salts are a group of heteroaromatic compounds. They are colorless or very slightly colored and freely soluble in water due to their ionic character. They form on reduction highly colored water insoluble compounds called formazans (i.e. groups of Formula IV). A number of tetrazolium salts are commercially available or are reported in the literature, which will form a colored precipitate when exposed to a leaving group described above. Representative tetrazolium salts include the following:

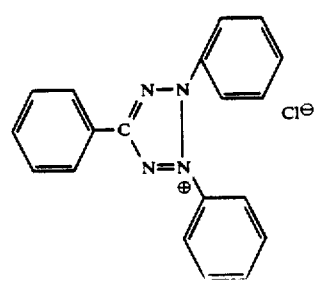

-continued
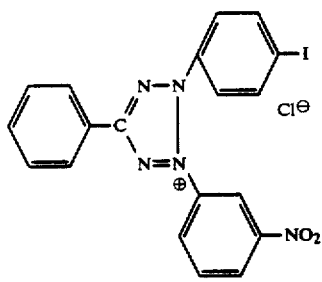
2-p-iodophenyl-3-p-nitrophenyl-5-phenyl-2H-tetrazolium chloride (INT)
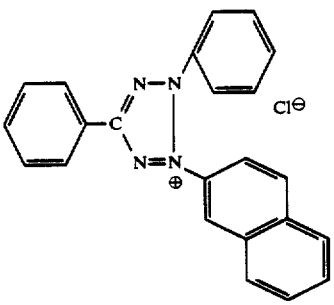
3-naphthyl-2,5-diphenyl-2H-tetrazolium chloride (TV)
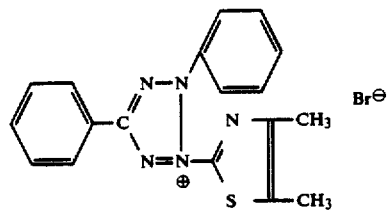
3-(4,5-dimethyl-2-thiazolyl)-2,5-diphenyl-2H-tetrazolium bromide (MTT)
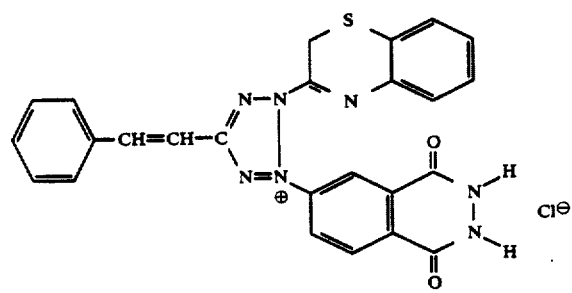
2-(2-benzthiazolyl)-3-(4-phthalylhydrazidyl)-5-styryl-2H-tetrazolium bromide (BPST)
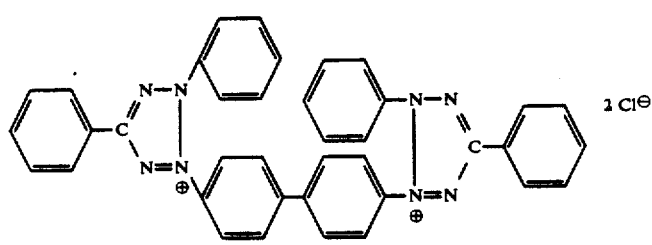
3,3'-(4,4'-biphenylene)-bis-(2,5-diphenyl-2H-tetrazolium chloride (NT)

-continued

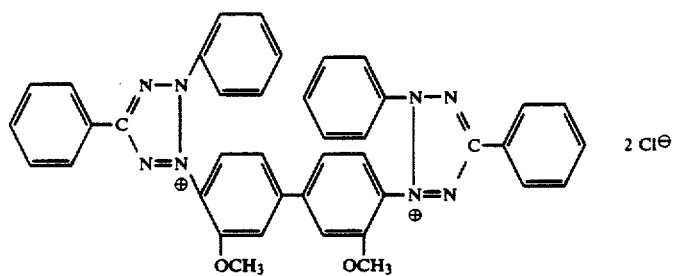
3,3'-(3,3'-dimethoxy-4,4'-biphenylene)-bis-(2,5-diphenyl-2H-tetrazolium chloride (BT)

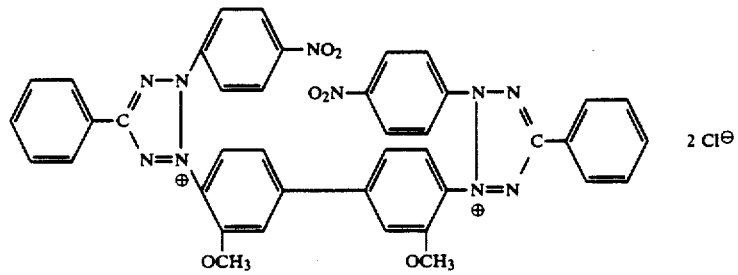
3,3'-(3,3'-dimethoxy-4,4'-biphenylene)-bis-(2-p-nitrophenyl-5-phenyl-2H-tetrazolium chloride (NBT)

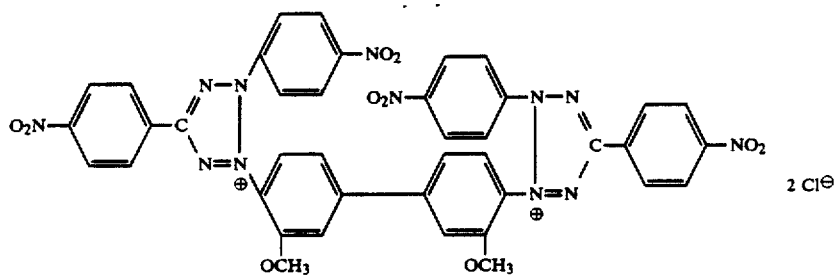
3,3'-(3,3'-dimethoxy-4,4'-biphenylene)-bis-(2,5-p-nitrophenyl-2H-tetrazolium chloride (TNBT)

The redox potentials ($E'_o$) of the tetrazolium salts shown above are provided below for various pH values.

| Tetrazolium | $E_o'$ (volts) | pH |
|---|---|---|
| TNBT | −0.05 | 7.2 |
| NBT | −0.05 | 7.2 |
| INT | −0.09 | 7.2 |
| MTT | −0.11 | 7.2 |
| NT | −0.17 | 7.2 |
| NT | −0.22 | 7.6 |
| BT | −0.16 | 7.2 |
| BT | −0.23 | 7.6 |
| TT | −0.49 | 7.2 |
| TT | −0.37 | 7.6 |
| TT | −0.44 | 7.0 |

General Definitions

As used herein, the term "halo" or "halogen" refers to chloro, bromo, fluoro, and iodo groups, while the term "$C_1$ to $C_6$ alkyl" refers to lower alkyl groups including methyl, ethyl, propyl, isopropyl, butyl and the like.

"Conjugate Acid" is the protonated species of the leaving group anion.

Assay Methods and Kits

Assays can be performed using the cephalosporin derivatives and tetrazolium salts described above. In one such assay, the presence of β-lactamase producing bacteria can be detected by introducing into a sample of biological fluid suspected of containing such bacteria a compound of formula I and a compound of formula II. If β-lactamase producing bacteria are present, compound I will be cleaved, liberating a reducing group of formula III. The reducing group will reduce the tetrazolium salt of formula II to produce a colored formazan compound of formula IV.

Kits for assays for β-lactamase producing bacteria include compounds of formulae I and II either in the same or different solutions, or provided in dry form to be made into solution. The kit can include an appropriate buffer or dilution solution. In addition, an electron carrier (or accelerator) is desirable in the kit to introduce into the reaction mixture of the compounds of Formulae I and II. An accelerator is a molecular species which is transiently reduced by the leaving group, and then immediately reoxidized by release of electrons to the tetrazolium salt. The accelerator aids in the transfer of electrons from the leaving group to the tetrazolium salt. The use of an accelerator greatly increases the speed of the reaction. Preferred accelerators include phenazine methosulfate (PMS), phenazine ethosulfate, 1-alkoxy phenazinium methosulfate, and Meldola's Blue.

The reagents described above can also be used in assays where β-lactamase is used as a label for a specific binding member. "Specific binding member" means any substance or group of substances which has a specific binding affinity for a particular ligand and virtually none other. A "ligand" is the substance or group of substances the presence or amount of which is to be determined in the sample. For instance, the specific binding member can be an antibody, and the ligand can be the drug, protein or the like to be detected in the sample which binds to the antibody. Conversely, the specific binding member can be a drug, protein or the like which binds to the antibody to be detected in the sample. Other examples of specific binding member/ligand pairs include enzyme/enzyme receptors, carbohydrate/lectin, complementary nucleic acid strands, and the like.

The labelled specific binding member can be used in assays for ligand in a variety of different ways. The assay can be a heterogeneous or homogeneous assay, forward or reverse, or a liposome lytic immunoassay.

Assay kits for ligands employing reagents of this invention include β-lactamase conjugated to a specific binding member, a tetrazolium salt of formula II and a substrate of formula I. Appropriate buffer solutions and the like can also be included. In addition, an electron carrier (or accelerator) is desirable to aid in the transfer of electrons from the leaving group to the tetrazolium salt.

The examples which follow illustrate the invention, and are not intended to limit it. In Example 1, an assay employing a substrate of Formula I (7-thiophenylacetamido-3-thioacetoxymethyl-3-cephem-4-carboxylate sodium salt) is described. In Example 2, a β-hCG assay using a substrate of Formula I is described. In Example 3, another β-hCG assay is described. In Example 4, the sensitivity of the reagents of this invention is demonstrated. In Example 5, other assays for β-lactamase are described.

EXAMPLE 1

Assay for β-Lactamase Producing Bacteria

A. Synthesis of 7-Thiophenylacetamido-3-thioacetoxymethyl-3-cephem-4-carboxylate Sodium Salt

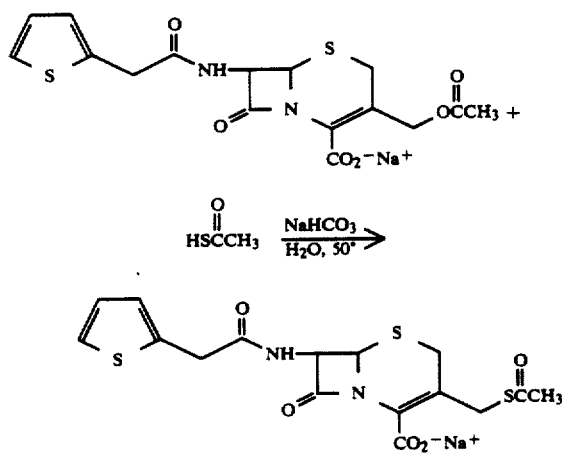

As illustrated in the reaction scheme above, thiolacetic acid (0.776 g, 10.2 mmol) and sodium bicarbonate (0.857 g, 10.2 mmol) were dissolved in $H_2O$ (30 ml) and warmed to 50° C. The warm solution was filtered through silica gel, and added to a solution of cephalothin (1.43 g, 3.4 mmol) in $H_2O$ (10 ml). The reaction mixture was stirred for 31 hours at 50° C. After cooling to room temperature, the water was removed by vacuum, and the residue was dissolved in methyl alcohol. Crude product was precipitated by addition of diethyl ether, and the solid was triturated with ethyl acetate. Precipitation and trituration were repeated until pure 7-thiophenylacetamido-3-thioacetoxymethyl-3-cephem-4-carboxylate sodium salt (1.16 g) was obtained.

mp 207–210 dec.

IR (KBr, $cm^{-1}$) 3290, 1750, 1650, 1600, 1530, 1400, 1355.

NMR ($D_2O,\delta$): 2.30(3H,s); 3.45(2H,dd); 3.85(2H,dd); 3.90(2H,s); 5.05(1H,d); 5.60(1H,d); 7.00(2H,d); 7.30(1H,t).

B. Assay for β-Lactamase

Whatman #1 filter paper disks were impregnated with 0.05M phosphate buffer pH 7.0 and dried. The disks were saturated with a solution of $1\times10^{-3}$M INT, $2.5\times10^{-5}$M PMS, and $2.5\times10^{-3}$M the cephalosporin substrate of Part A in deionized water. The disks were dried at room temperature in the dark under high vacuum. Strips cut from these disks were then dipped in varying concentrations of β-lactamase from *Enterobacter cloacae*. A visible color change was observed with the strips turning reddish-pink. The greatest color change was observed with $1\times10^{-5}$M β-lactamase ($5\times10^{-10}$ moles deposited on the strip) with the limit of detectability at $1\times10^{-8}$M ($5\times10^{-13}$ moles deposited on the strip).

C. Control Experiment

As a control, solutions were prepared as described in part B above without β-lactamase, and analyzed as described above. No color change was observed with strips dipped in deionized water without enzyme.

EXAMPLE 2

β-hCG Assay Using β-lactamase/anti β-hCG IgG conjugate

A. Production of Anti β-hCG IgG

Antibody to β-hCG was produced by inoculating goats with the purified β subunit of hCG combined with an adjuvant. This emulsion was then injected subcutaneously in the axillary and inguinal regions. A second injection was given 30 days later, and a third injection given 30 days after that. Two weeks later, a blood sample was drawn, and the serum tested for the presence of anti β-hCG IgG. When the antibody titer reached an acceptable level, the goat was put on a production bleeding schedule to harvest large volumes of serum. This serum was then accumulated and pooled for purification.

The purification was accomplished by passing the serum over a β-subunit specific affinity column. β-specific IgG was then collected, protein concentration calculated, and the antibody diluted to 3.5 mg/ml.

B. β-lactamase/Anti β-hCG IgG Conjugation with SMCC

β-lactamase (P-99 from Porton Products) was conjugated to anti β-hCG IgG (Example 2, part A) using succinimidyl 4-(N-maleimidomethyl)cyclohexane-1- carboxylate (SMCC) from Pierce. Reduction of the antibody to generate thiols was accomplished by incubation of antibody (2 mg) at 3.5 mg/ml in 25 mM dithiothreitol (DTT) for 30 minutes at room temperature while rotating the mixture at 100 RPM. The DTT was then removed by passing the reduced antibody over a gel filtration (Sephadex G-25) column, collecting and pooling the antibody containing fractions.

β-lactamase (2 mg) at 2.0 mg/ml was modified by incubation with a 50 molar excess of SMCC in N,N-dimethylformamide (DMF) for 30 minutes at room temperature while rotating the mixture at 100 RPM. The unreacted reactants were then removed by passing the derivatized enzyme over a gel-filtration (Sephadex G-25) column, collecting and pooling the enzyme containing fractions.

The reduced antibody and modified enzyme were then combined at a molar ratio of 2.5 enzyme:1 antibody, and incubated 18 hours at 5° C. while rotating the mixture at 100 RPM. Unreacted thiols were then capped to block any further conjugation/aggregation by the addition of 100 ul of 5 mM N-ethylmaleimide to 1.5 ml of conjugate. Conjugates were then stored at 5° C. until utilized.

C. Preparation of Beads With Affinity Purified Goat Anti-β-hCG

5/16" polystyrene beads (from Evco) were ground to produce a rough surface. Affinity purified goat anti β-hCG (Example 2, part A) was adsorbed to the surface of the beads and the beads overcoated with a gelatin-sucrose mixture to block nonspecific binding.

D. Assay for β-hCG

A standard curve (FIG. 1) for β-hCG was generated using β-lactamase/anti β-hCG IgG conjugate of Example 2, Part B. This assay was performed in a heterogeneous bead format and used thiol-substituted cephalosporin (TAC) from Example 1 part A as the substrate.

One of the beads from part C was added to each well of a reaction tray containing 300 ul of β-hCG standards of known concentration. The beads were incubated with the standards for one hour at room temperature while the reaction tray was rotated at 180 RPM. The beads were washed with 3 pulses of 5 ml each of phosphate buffer to wash away unbound analyte. β-lactamase/anti β-hCG IgG conjugate (300 ul 4.0 ug/ml) of Example 2 part B was added to each well of the reaction tray. The beads were incubated with the conjugate for one hour at room temperature while the reaction tray was rotated at 180 RPM. The beads were then washed with 3 pulses of 5 ml each of phosphate buffer to wash away unbound conjugate. The beads were transferred to clean reaction tubes to which substrate mixture (1.0 ml) was added. The substrate mixture of $1.3 \times 10^{-3}$M iodonitrotetrazolium violet (INT), $3.2 \times 10^{-3}$M TAC, and $3.2 \times 10^{-5}$M phenazine methosulfate (PMS) in 0.1M NaPO$_4$, 0.1M NaCl, 0.32% BSA pH 7.0 was prepared. The beads were incubated with the substrate mixture for one hour at room temperature while the reaction tubes were rotated at 180 RPM. The substrate mixture was then transferred to a clean cuvette, and the absorbance at 500 nm was read in a UV/Vis spectrophotometer. A$_{500}$ readings were then plotted against the standard concentrations to generate the standard curve of FIG 1.

EXAMPLE 3

Assay for β-hCG Using β-lactamase/Anti β-hCG IgG Conjugates With 30-atom Linker

A. Preparation of β-lactamase/Anti β-hCG IgG Conjugate With 30-atom Linker

β-lactamase (P-99 from Porton Products) was conjugated to anti β-hCG IgG (Example 2, part A) using succinimidyl 4-(N-maleimidomethyl) cyclohexyl tricaproamido-1-carboxylate (a 30 atom linker group) disclosed in U.S. patent application Ser. No. 114,930 filed Oct. 30, 1987 which was incorporated herein by reference. Reduction of the antibody to generate thiols was accomplished by incubation of antibody (2 mg) at 3.5 mg/ml in 25 mM dithiothreitol (DTT) for 30 minutes at room temperature while rotating the mixture at 100 RPM. The DTT was then removed by passing the reduced antibody over a gel filtration (Sephadex G-25) column, and the antibody-containing fractions were collected and pooled.

β-lactamase (2 mg) at 2.0 mg/ml was modified by incubation with a 50 molar excess of 30-atom linker arm in N,N-dimethylformamide (DMF) for 30 minutes at room temperature while the mixture was rotated at 100 RPM. The unreacted linker was then removed by passing the derivatized enzyme over a gel-filtration (Sephadex G-25) column, and the enzyme-containing fractions were collected and pooled.

The reduced antibody and modified enzyme were then combined at a molar ratio of 2.5 enzyme:1 antibody, and incubated 18 hours at 5° C. while the mixture was rotated at 100 RPM. Unreacted thiols were then capped to block any further conjugation/aggregation by the addition of 100 ul of 5 mM N-ethylmaleimide to 1.5 ml of conjugate. Conjugates were then stored at 5° C. until utilized.

B. Assay for β-hCG Using β-lactamase/Anti β-hCG IgG Conjugate With 30-atom Linker The assay of example 2 can be repeated using the conjugate of Example 3, part A instead of the conjugate of Example 2, part B.

EXAMPLE 4

UV/Vis Spectrophotometric Assay

In each of several cuvettes, 1) an aliquot (2.0 ml) of a solution containing $2 \times 10^{-3}$M INT, 0.05M phosphate buffer, and 1% bovine serum albumin pH 7.0, 2) $1 \times 10^{-2}$M thiol-substituted cephalosporin (TAC) from Example 1, part A in deionized water (1.0 ml), and 3) $1 \times 10^{-3}$M phenazine methosulfate (PMS) in deionized water (0.1 ml) were combined. To each cuvette, a β-lactamase solution (0.1 ml) at a concentration ranging from $5 \times 10^{-5}$M to $1 \times 10^{-7}$M in deionized water was added. The absorbance of the reaction mixture in each cuvette was monitored at 500 nm during a 90 minute period. The results were then compared to the absorbance of a control reaction mixture having the same concentrations of INT, TAC and PMS, but without enzyme. Sensitivity down to $1 \times 10^{-10}$ moles of β-lactamase was observed for this system.

EXAMPLE 5
Other Assays for β-Lactamase
A. General

Other assays were performed for β-lactamase using not only the tetrazolium salt and the substrate of Example 1, but other tetrazolium salts and substrates. The synthesis of the other substrates is described in parts C through G of this example. The assay method is described in part B of this example, and the data obtained are reported in Table I.

B. Assay Method

An assay was performed by combining in a reaction vessel a solution of a tetrazolium salt, a β-lactamase substrate, and β-lactamase with or without an accelerator and bovine serum albumin (BSA) as indicated in Table I. During a period of time in which the reaction takes place (i.e. the "run time" indicated in Table I), the absorbance of the reaction mixture was monitored at the wavelength indicated in the column captioned "wavelength". The maximum absorbance was recorded for each mixture tested. For each mixture, a control solution was prepared which was identical to the reaction mixture, except that no β-lactamase was added. The absorbance of the control was recorded in each case at 500 nm, and the ratio of the maximum absorbance to the control solution absorbance was recorded (last column in Table I captioned "Ratio"). A ratio greater than 1.0 indicated an observable reaction in the reaction mixture in the "run time". Unless indicated by an asterisk (*), the β-lactamase used was Sigma Chemical Co. P-0389. In the experiments indicated by the asterisk (*), β-lactamase from Porton Products (P-99) was used.

C. Synthesis of 7-Thiophenylacetamido-3-(4-bromothiophenoxy)methyl-3-cephem-4-carboxylate Sodium Salt

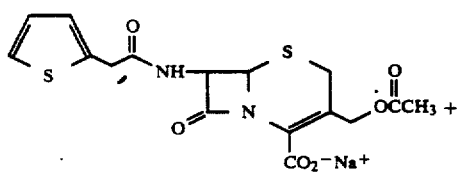

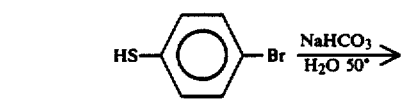

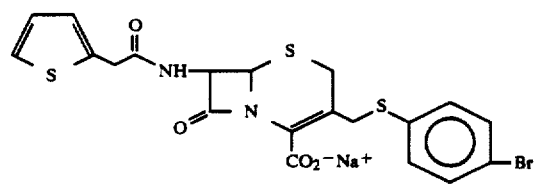

As shown in the reaction scheme above, 4-bromothiophenol (1.285 g, 6.8 mmol) and sodium bicarbonate (0.571 g, 6.8 mmol) were stirred in water (20 ml) and heated to 50° C. The mixture was filtered through silica gel, and the filtrate was added to cephalothin (0.948 g, 2.27 mmol) in water (5 ml). The mixture was stirred for 30 hours at 50° C. The solvent was removed under vacuum. The residue was dissolved in methanol, and diethyl ether was added to precipitate pure 7-thiophenylacetamido-3-(4-bromothiophenoxy)methyl-3-cephem-4-carboxylate sodium salt.

mp 163–171 dec.

IR (KBr, cm$^{-1}$) 3420, 1750, 1650, 1600, 1400, 1090, 1010, 810, 700.

NMR (DMSO-$d_6$, δ): 3.35(2H,dd); 3.72(2H,s); 4.22(2H,dd); 4.75(1H,d); 5.40(1H,dd); 6.85(2H,t); 7.35(5H,m); 8.93(1H,d).

D. Synthesis of 7-Thiophenylacetamido-3-(3-hydroxy-2-thiopyridyl)methyl-3-cephem-4-carboxylate Sodium Salt

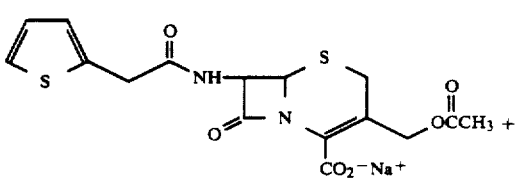

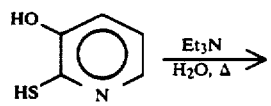

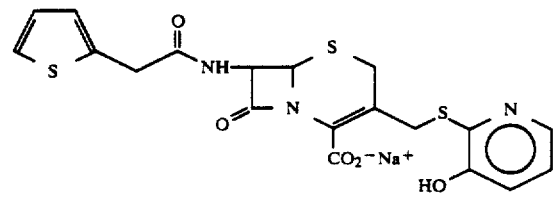

As illustrated in the reaction scheme above, cephalothin (1.06 g, 2.5 mmol) was added to a solution of 2-mercapto-3-pyridinol (0.322 g, 2.5 mmol) and triethylamine (0.257 g, 2.5 mmol) in H$_2$O (50 ml). The mixture was stirred for six hours at 70° C. The water was removed under reduced pressure. The residue was dissolved in 1:1 MeOH/benzene, and product was precipitated by addition of diethylether. Two further repetitions of this procedure yielded pure 7-thiophenylacetamido-3-(3-hydroxy-2-thiopyridyl)methyl-3 -cephem-4-carboxylate sodium salt (0.677 g).

mp 175–184 dec.

IR (KBr, cm$^{-1}$) 3260, 1740, 1550, 1350, 690.

NMR (DMSO-$d_6$, δ): 3.72(2H,dd); 3.76(2H,s); 4.40(2H,s); 5.28(1H,dd); 5.50(1H,d); 6.58(1H,d); 6.90-7.03(3H,m); 7.30(1H,d); 7.38(1H,d); 9.18(1H,d).

E. Synthesis of 7-Thiophenylacetamido-3-thiobenzoyl methyl-3-cephem-4-carboxylate Sodium Salt

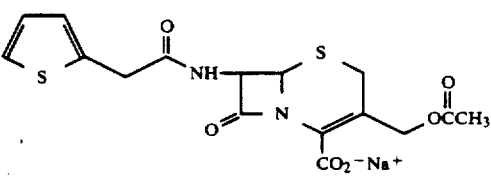

-continued

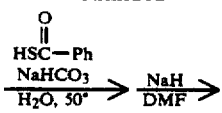

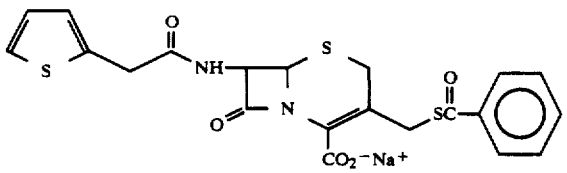

Thiobenzoic acid (1.41 g, 10.2 mmol) and sodium bicarbonate (0.857 g, 10.2 mmol) were stirred in 30 ml of H₂O and heated to 50° C. The mixture was filtered through silica gel, and the filtrate was added to cephalothin (1.43 g, 3.4 mmol) in 20 ml of H₂O. The reaction mixture was stirred for 20 hours at 50° C. 7-Thiophenylacetamido-3-thiobenzoylmethyl-3-cephem-4-carboxylic acid (0.791 g) was collected by filtration. 50 mg of this material was dissolved in DMF (2 ml). Sodium hydride (4.4 mg. 0.11 mmol) was added, and the mixture was stirred for two hours, filtered, and dried under vacuum. The residue was dissolved in water, refiltered and lyophilized to yield pure 7-thiophenylacetamido-3-thiobenzoylmethyl-3-cephem-4-carboxylate sodium salt.

mp 239–241 dec.

IR (KBr, cm⁻¹) 3400, 3280, 1736, 1588, 1526, 1345, 1185, 910, 685.

NMR (DMSO-d₆, δ): 3.35(2H,dd); 3.78(2H,s); 4.25(2H,dd); 4.96(1H,d); 5.47(1H,dd); 6.95(2H,t); 7.35(1H,d); 7.58(2H,t); 7.71(1H,t); 7.96(2H,d); 9.04(1H,d).

F. Synthesis of 7-Thiophenylacetamido-3-(4-aminothiophenoxy)methyl-3-cephem-4-carboxylate Sodium Salt

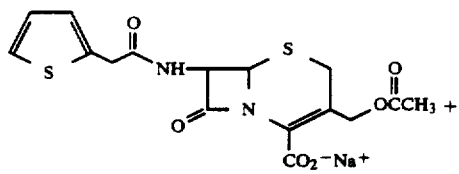

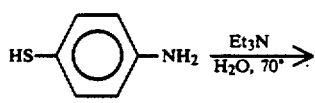

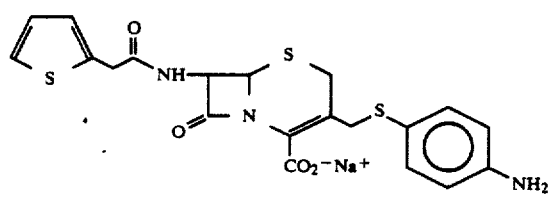

As illustrated in the reaction scheme above, 4-aminothiophenol (0.580 g, 4.6 mmol) was dissolved in DMF (10 ml). This solution was added to water (100 ml) containing triethylamine (4.6 mmol, 0.465 g). Cephalothin (1.94 g, 4.6 mmol) was added, and the mixture was brought to 70° C. and stirred for six hours. The mixture was cooled to room temperature, and the water was removed by vacuum. The residue was twice precipitated from 1:1 MeOH/benzene by addition of diethyl ether to yield pure 7-thiophenylacetamido-3-(4-aminothiophenoxy)methyl-3-cephem-4-carboxylate sodium salt (1.026 g).

mp 169–175.

IR (KBr, cm⁻¹) 3360, 3020, 1740, 1580, 1490, 1380, 1180.

NMR (DMF-d₇, δ): 3.33(2H,dd); 3.52(2H,s); 4.38(2H,dd); 4.93(1H,d); 5.62(1H,dd); 6.62(2H,d); 6.95(2H,t); 7.17(2H,d); 7.40(1H,d); 8.95(1H,dd).

G. Synthesis of 7-Thiophenylacetamindo-3-(S-cysteinyl)methyl-3-cephem-4-carboxylate Sodium Salt

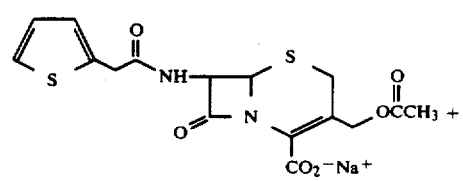

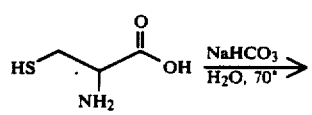

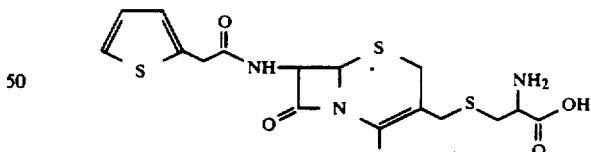

L-Cysteine (2.10 g, 17.3 mmol) and sodium bicarbonate (1.45 g, 17.3 mmol) were dissolved in water (50 ml) and heated to 70° C. The warm solution was filtered through silica gel into cephalothin (2.42 g, 5.77 mmol) in water (10 ml). The combined solution was stirred for 30 hours at 70° C. The solvent was removed under reduced pressure. The residue was dissolved in DMF, and 2-propanol was added to precipitate 7-thiophenylacetamido-3-(S-cysteinyl)methyl-3-cephem-4-carboxylate sodium salt.

TABLE I

| Experiment No. | Tetrazolium Salt | β-Lactamase Substrate | PMS | BSA | β-Lactamase | Run Time (minutes) | Maximum Absorbance (Absorbance Units) | Control Absorbance (Absorbance Units) | Ratio | Wavelength (nm) |
|---|---|---|---|---|---|---|---|---|---|---|
| 1 | NBT (1 ml; $2 \times 10^{-3}$M) | Ex. 5; Part D (1 ml; $5 \times 10^{-2}$M) | 1 ml; $1 \times 10^{-2}$M | 5% | 1 ml; $2 \times 10^{-8}$M | 120 | 1.9 | 1.2 | 1.58 | 530 |
| 2 | NBT (1 ml; $2 \times 10^{-3}$M) | Ex. 5; Part F (1 ml; $5 \times 10^{-2}$M) | No | No | 1 ml; $1 \times 10^{-6}$M | 30 | None | None | — | 530 |
| 3 | NBT (2 ml; $2 \times 10^{-3}$M) | Ex. 5; Part F (1 ml; $3.8 \times 10^{-3}$M) | No | 5% | 0.1 ml; $1.79 \times 10^{-4}$M | 120 | 0.058 | 0.038 | 1.53 | 530 |
| 4 | NBT (2 ml; $2 \times 10^{-3}$M) | Ex. 5; Part C (1 ml; $3.8 \times 10^{-3}$M) | No | 5% | 0.1 ml; $1.79 \times 10^{-4}$M | 30 | None | — | — | 530 |
| 5 | INT (1 ml; $1 \times 10^{-3}$M) | Ex. 5; Part C (1 ml; $1 \times 10^{-4}$M) | No | 1% | 0.01 ml; $3.3 \times 10^{-7}$M | 15 | None | — | — | 500 |
| 6 | INT (2 ml; $2 \times 10^{-3}$M) | Ex. 5; Part F (1 ml; $3.8 \times 10^{-3}$M) | No | 1% | 0.1 ml; $1.79 \times 10^{-4}$M | 90 | 0.190 | 0.123 | 1.54 | 500 |
| 7 | INT (2 ml; $2 \times 10^{-3}$M) | Ex. 5; Part F (1 ml; $3.8 \times 10^{-3}$M) | 0.1 ml; $1 \times 10^{-2}$M | 1% | 0.1 ml; $1.79 \times 10^{-4}$M | 60 | 0.915 | 0.681 | 1.34 | 500 |
| 8 | INT (2 ml; $2 \times 10^{-3}$M) | Ex. 1, Part A (1 ml; $1 \times 10^{-2}$M) | No | 1% | 0.1 ml; $5 \times 10^{-5}$M | 60 | 0.10 | 0.20 | — | 500 |
| 9 | INT (2 ml; $2 \times 10^{-3}$M) | Ex. 1, Part A (1 ml; $1 \times 10^{-2}$M) | 0.1 ml; $1 \times 10^{-2}$M | 1% | 0.1 ml; $5 \times 10^{-5}$M | 60 | >3.0 | 1.82 | >1.65 | 500 |
| 10 | NBT (2 ml; $2 \times 10^{-3}$M) | Ex. 1; Part A (1 ml; $1 \times 10^{-2}$M) | No | 1% | 0.1 ml; $5 \times 10^{-5}$M | 60 | PPT | 0.22 | — | 530 |
| 11 | NBT (2 ml; $2 \times 10^{-3}$M) | Ex. 1; Part A (1 ml; $1 \times 10^{-2}$M) | 0.1 ml; $1 \times 10^{-2}$M | 1% | 0.1 ml; $5 \times 10^{-5}$M | 60 | 1.25 | 1.02 | 1.23 | 530 |
| 12 | INT 2 ml; $2 \times 10^{-3}$M | Ex. 1; Part A (1 ml; $1 \times 10^{-2}$M) | No | 1% | 0.1 ml; $5 \times 10^{-5}$M | 60 | 0.11 | 0.10 | 1.1 | 500 |
| 13 | INT (2 ml; $2 \times 10^{-3}$M) | Ex. 1; Part A (1 ml; $1 \times 10^{-2}$M) | 0.1 ml; $1 \times 10^{-2}$M | 1% | 0.1 ml; $5 \times 10^{-5}$M | 60 | 73.0 | 0.98 | 73.06 | 500 |
| 14 | INT (2 ml; $2 \times 10^{-3}$M) | Ex. 1; Part A (1 ml; $1 \times 10^{-2}$M) | 0.1 ml; $1 \times 10^{-3}$M | 1% | 0.1 ml; $5 \times 10^{-5}$M | 60 | 1.52 | 0.36 | 4.22 | 500 |
| 15 | INT (2 ml; $2 \times 10^{-3}$M) | Ex. 1; Part A (1 ml; $5 \times 10^{-2}$M) | 0.1 ml; $1 \times 10^{-2}$M | 1% | 0.1 ml; $5 \times 10^{-5}$M | 60 | 0.88 | 0.24 | 3.67 | 500 |
| 16 | INT (2 ml; $2 \times 10^{-3}$M) | Ex. 1; Part A (1 ml; $1 \times 10^{-3}$M) | 0.1 ml; $1 \times 10^{-2}$M | 1% | 0.1 ml; $5 \times 10^{-5}$M | 60 | 0.15 | 0.10 | 1.50 | 500 |
| 17 | INT (2 ml; $2 \times 10^{-3}$M) | Ex. 1; Part A (1 ml; $1 \times 10^{-2}$M) | 0.1 ml; $1 \times 10^{-2}$M | 1% | 0.1 ml; $5 \times 10^{-5}$M | 60 | 1.95 | 0.43 | 4.53 | 500 |
| 18 | INT (2 ml; $2 \times 10^{-3}$M) | Ex. 1; Part A (1 ml; $1 \times 10^{-2}$M) | 0.1 ml; $1 \times 10^{-3}$M | 1% | 0.1 ml; $1 \times 10^{-5}$M | 60 | 1.60 | 0.43 | 3.72 | 500 |
| 19 | INT (2 ml; $2 \times 10^{-3}$M) | Ex. 1; Part A (1 ml; $1 \times 10^{-2}$M) | 0.1 ml; $1 \times 10^{-3}$M | 1% | 0.1 ml; $1 \times 10^{-6}$M | 60 | 0.61 | 0.43 | 1.42 | 500 |
| 20 | INT (2 ml; $2 \times 10^{-3}$M) | Ex. 1; Part A (1 ml; $1 \times 10^{-2}$M) | 0.1 ml; $1 \times 10^{-3}$M | 1% | 0.1 ml; $1 \times 10^{-7}$M | 60 | 0.45 | 0.43 | 1.05 | 500 |
| 21 | INT (2 ml; $2 \times 10^{-3}$M) | Ex. 1; Part A (1 ml; $1 \times 10^{-2}$M) | 0.1 ml; $1 \times 10^{-3}$M | 1% | 0.1 ml; $1 \times 10^{-5}$M | 60 | 0.27 | 0.82 | — | 500 |
| 22 | INT (2 ml; $2 \times 10^{-3}$M) | Ex. 1; Part A (1 ml; $1 \times 10^{-2}$M) | 0.1 ml; $1 \times 10^{-3}$M | 1% | 0.1 ml; $1 \times 10^{-6}$M | 60 | 0.67 | — | — | 500 |
| 23 | INT (2 ml; $2 \times 10^{-3}$M) | Ex. 1; Part A (1 ml; $1 \times 10^{-2}$M) | 0.1 ml; $1 \times 10^{-3}$M | 1% | 0.1 ml; $1 \times 10^{-7}$M | 60 | 0.76 | — | — | 500 |
| 24 | INT (2 ml; $2 \times 10^{-3}$M) | Ex. 1; Part A (1 ml; $1 \times 10^{-2}$M) | 0.1 ml; $1 \times 10^{-3}$M | 1% | 0.1 ml; $1 \times 10^{-5}$M | 60 | 1.31 | 0.52 | 2.52 | 500 |
| 25 | INT (2 ml; $2 \times 10^{-3}$M) | Ex. 1; Part A (1 ml; $1 \times 10^{-2}$M) | 0.1 ml; $1 \times 10^{-3}$M | 1% | 0.1 ml; $1 \times 10^{-5}$M | 60 | 2.30 | 0.82 | 2.82 | 500 |
| 26 | INT (2 ml; $2 \times 10^{-3}$M) | Ex. 1; Part A (1 ml; $1 \times 10^{-2}$M) | 0.1 ml; $1 \times 10^{-3}$M | 1% | 0.1 ml; $1 \times 10^{-5}$M | 60 | 2.34 | 0.88 | 2.66 | 500 |

TABLE I-continued

| Experiment No. | Tetrazolium Salt | β-Lactamase Substrate | PMS | BSA | β-Lactamase | Run Time (minutes) | Maximum Absorbance (Absorbance Units) | Control Absorbance (Absorbance Units) | Ratio | Wavelength (nm) |
|---|---|---|---|---|---|---|---|---|---|---|
| 27 | MTT (2 ml; $2 \times 10^{-3}$M) | Ex. 1; Part A (1 ml; $1 \times 10^{-2}$M) | 0.1 ml; $1 \times 10^{-3}$M | 1% | 0.1 ml; $1 \times 10^{-5}$M | 60 | >3.0 | 0.96 | >3.13 | 564 |
| 28 | INT (2 ml; $2 \times 10^{-3}$M) | Ex. 1; Part A (1 ml; $1 \times 10^{-2}$M) | 0.1 ml; $1 \times 10^{-3}$M | 1% | 0.1 ml; $1 \times 10^{-5}$M* | 60 | >3.0 | 0.76 | >3.95 | 500 |
| 29 | INT (2 ml; $2 \times 10^{-3}$M) | Ex. 1; Part A (1 ml; $1 \times 10^{-2}$M) | Ferrocene** 0.1 ml; $1 \times 10^{-3}$M | 1% | 0.1 ml; $1 \times 10^{-5}$M* | 60 | 0.35 | 0.20 | 1.75 | 500 |
| 30 | NBT (2 ml; $2 \times 10^{-3}$M) | Ex. 1; Part A (1 ml; $1 \times 10^{-2}$M) | 0.1 ml; $1 \times 10^{-3}$M | 1% | 0.1 ml; $1 \times 10^{-5}$M* | 30 | 0.60 | 0.24 | 2.50 | 500 |
| 31 | INT (2 ml; $2 \times 10^{-3}$M) | Ex. 1; Part A (1 ml; $1 \times 10^{-2}$M) | 0.1 ml; $1 \times 10^{-3}$M | 1% | 0.1 ml; $1 \times 10^{-5}$M* | 30 | 1.87 | 0.43 | 4.35 | 500 |
| 32 | INT (2 ml; $2 \times 10^{-3}$M) | Ex. 1; Part A (1 ml; $1 \times 10^{-2}$M) | 0.1 ml; $1 \times 10^{-3}$M | 1% | 0.1 ml; $1 \times 10^{-5}$M* | 30 | 1.86 | 0.40 | 4.65 | 500 |
| 33 | INT (2 ml; $2 \times 10^{-3}$M) | Ex. 1; Part A (1 ml; $1 \times 10^{-2}$M) | 0.1 ml; $1 \times 10^{-3}$M | 2% | 0.1 ml; $1 \times 10^{-5}$M* | 30 | 2.19 | 0.56 | 3.91 | 500 |
| 34 | INT (2 ml; $2 \times 10^{-3}$M) | Ex. 1; Part A (1 ml; $1 \times 10^{-2}$M) | 0.1 ml; $1 \times 10^{-3}$M | 1% | 0.1 ml; $1 \times 10^{-5}$M* | 30 | 1.74 | 0.40 | 4.35 | 500 |
| 35 | INT (2 ml; $2 \times 10^{-3}$M) | Ex. 5, Part E (1 ml; $1 \times 10^{-2}$M) | 0.1 ml; $1 \times 10^{-3}$M | 1% | 0.1 ml; $1.10^{-5}$M* | 30 | 0.68 | 0.51 | 1.33 | 500 |

**Ferrocene was used as the accelerator instead of PMS.

EXAMPLE 6

Assay for Urinary Tract Infection

A. Preparation of Urinary Tract Infection Antibodies

Antibodies to urinary tract infectious microorganisms were raised by innoculating rabbits with emulsions containing heat inactivated microorganisms including *Pseudomonas auruginosa*, *Streptococcus D*, *Escherichia coli*, *Proteus mirabilis*, and *Klebsiella pneumoniae*, each rabbit being injected with a different microorganism. Rabbits were injected with the emulsions subcutaneously and intramuscularly, later injections were given 21 days later, and third injections were given 21 days after that. One week later, blood samples were drawn and the serum tested for the presence of antibodies to the antigen pool described above. When the antibody titer reached an acceptable level, each rabbit was put on a production bleeding schedule to harvest sufficient volumes of serum for purification of antibodies to a particular urinary tract infectious microorganism. The serum was purified by passing the serum through a DE52 (Whatman) anion exchange column to separate IgG from other proteins. The antibody-containing fractions were then collected for each rabbit, and the protein concentration calculated. The antibodies against the various microorganisms were then pooled, and the antibody pool diluted to 1.1 mg/ml.

B. Preparation of Microparticles With Antibacterial Antibody

The rabbit antibacterial IgG from part A above was coupled using EDC (1-ethyl-3-(3-dimethylaminopropyl)carbodiimide hydrochloride) to polystyrene carboxylated microparticles (Seradyn, Indianapolis, Ind.) as described in Avrameas, S. C. R., Acad. Sci. Paris, Vol. 262, p. 2543 (1966).

C. Preparation of Enzyme/Antibody Conjugates

A β-lactamase/antibacterial IgG conjugate was produced following the procedure outlined in Example 2, part B, substituting the antibacterial IgG produced in part A of this example for the β-HCG IgG of Example 2, part B for use in an assay for urinary tract infectious microorganisms described in part D below.

D. Assay for Urinary Tract Infectious Microorganisms

The microparticles from part B of this example coupled to antibody were suspended in a buffer (phosphate-buffered saline from Sigma Chemical and 0.1% sodium azide, pH 7.4 to a concentration of 0.08%). The microparticles (135 ul; 0.08% solids) were combined with a sample (1.0 ml) containing $10^7$ urinary tract infectious microorganisms per milliliter and EDTA/Sarcosyl (Sigma Chemical) extraction buffer (135 microliters), and the mixture was incubated at room temperature for five minutes. The mixture was then poured through a porous filter media (a Testpack device sold by Abbott Laboratories, Abbott Park, Ill.), and washed with buffer (1.0 ml of 1.0M guanidine-HCl, 1.0M NaCl, 0.1% Tween 20, 0.1% sodium azide; hereinafter "buffer A"). The β-lactamase antibacterial IgG conjugate solution of part C of this example (200 ul; 100 micrograms/ml) was added to the filter media and incubated at room temperature for five minutes The filter media was then washed with buffer A (1 ml). A solution (200 microliters) containing INT ($2.4 \times 10^{-4}$ molar), TAC ($4.8 \times 10^{-3}$ molar), PMS ($4.8 \times 10^{-4}$ molar) and sodium phosphate (0.1 molar) pH 7.0 was then passed through the filter media and incubated at room temperature for five minutes. The filter media was then washed with buffer A (1.0 ml) and visually compared to a control filter media which was treated in the same fashion, but without the bacteria. The bacteria-containing filter media was pink compared to the control which remained white, indicat-

What is claimed is:

1. A method for detecting β-lactamases in a sample, comprising:
   (a) exposing said sample to a β-lactamase substrate of formula I:

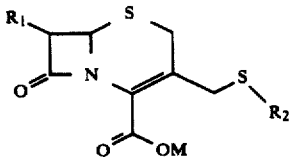

wherein $R_1$ is a group which maintains the ability of said substrate to be recognized as a substrate by β-lactamases and cleave the β-lactam ring; and
   $R_2$, together with the sulfur atom to which it is attached, form a leaving group which is released into solution, the conjugate acid of which has a pKa in water of less than 8, and M is hydrogen or a group I metal;
   (b) exposing said leaving group to a tetrazolium salt of formula II:

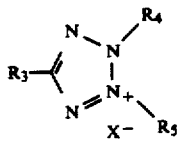

wherein $R_3$, $R_4$ and $R_5$ are independently selected from groups such that the redox potential of the resulting tetrazolium salt is 0 or lower volts; and
   X is an anion; whereby a colored precipitate is formed in the presence of the leaving group; and
   (c) monitoring said colored precipitate as an indicator of the presence of an active β-lactamase.

2. The method of claim 1 wherein said leaving group is selected from the group consisting of halo or amino substituted thiophenol; hydroxy, halo, or amino substituted mercapto pyridine; aliphatic or aromatic thiolcarboxylic acid; and mercapto amino acid.

3. The method of claim 2 wherein said leaving group is selected from the group consisting of p-bromo thiophenol, p-amino thiophenol, 2-mercapto-3 pyridinol, thiolacetic acid, thiobenzoic acid, and cysteine.

4. The method of claim 1 wherein $R_1$ is selected from the group consisting of amino,thiophene-2-acetamido, benzyl-2-acetamido, phenoxy-2-acetamido, D--aminoadipamido, 2-amino-2-phenylacetamido, tetrazolylacteamido, 4-pyridylthioacetamido, and a group of the formula:

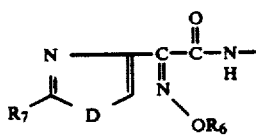

where $R_6$ is a lower aliphatic group, $R_7$ is an amino or alkylamino group, and D is an oxygen or sulfur atom.

5. The method of claim 4 wherein $R_1$ is selected from the group consisting of 2-(2-amino-4-thiazolyl)-2-(methoxyimino)acetamido-2-(2-amino-4-thiazolyl)-2-(carboxymethoxyimino)acetamido, and 2-(2-amino-4-thiazolyl)-2-(hydroxyimino)acetamido.

6. The method of claim 1 wherein $R_3$, $R_4$ and $R_5$ are independently selected from the group consisting of phenyl, p-iodophenyl, p-nitrophenyl, naphthyl, thiazolyl, alkylthiazolyl, benzothiazolyl, phthalylhydrazidyl, styryl, biphenyl, 3-biphenylene-2,5-diphenyltetrazolium chloride, 3-dimethoxy-4-biphenylene-2,5-diphenyltetrazolium chloride, 3-dimethoxy-4-biphenylene-2-p-nitrophenyl-5-phenyltetrazolium chloride and 3-dimethoxy-4-biphenylene-2,5-p-nitrophenyltetrazolium chloride.

7. An assay kit for detecting β-lactamase in a sample, comprising:
   (a) a β-lactamase substrate of formula I:

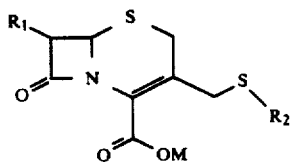

wherein $R_1$ is a group which maintains the ability of said substrate to be recognized as a substrate by β-lactamases and cleave the β-lactam ring; and
   $R_2$, together with the sulfur atom to which it is attached, form a leaving group which is released into solution, the conjugate acid of which has a pKa in water of less than 8, and M is hydrogen or a group I metal; and
   (b) a tetrazolium salt of Formula II:

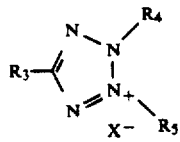

wherein $R_3$, $R_4$ and $R_5$ are independently selected from groups such that the redox potential of the resulting tetrazolium salt is 0 or lower volts; and
   X is an anion.

8. The assay kit of claim 7 further comprising an accelerator.

9. The assay kit of claim 8 wherein said accelerator comprises phenazine methosulfate.

10. The assay kit of claim 7 wherein said compounds of Formulae I and II are disposed on a solid phase.

11. The assay kit of claim 10 wherein said solid phase comprises a strip.

12. The assay kit of claim 7 wherein said leaving group is selected from the group consisting of an aliphatic or aromatic thiol; a halo or amino substituted thiophenol; hydroxy, halo, or amino substituted mercapto pyridines; aliphatic or aromatic thiolcarboxylic acids; a thiosulfonic acid; or a mercapto amino acid.

13. The assay kit of claim 7 wherein said leaving group is selected from the group consisting of p-bromo thiophenol; p-aminothiophenol; 2-mercapto-3-pyridinol; thiolacetic acid; thiobenzoic acid; and cysteine.

14. The assay kit of claim 7 wherein $R_1$ is selected from the group consisting of amino, thiophene-2-acetamido, benzyl-2-acetamido, phenoxy-2-acetamido, D-2-aminoadipamido, 2-amino-2-phenylacetamido, tetrazolylacteamido, 4-pyridylthioacetamido, and a group of the formula:

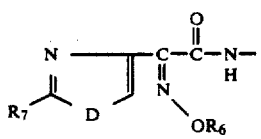

where $R_6$ is a lower aliphatic group, $R_7$ is an amino or alkylamino group, and D is an oxygen or sulfur atom.

15. The assay kit of claim 14 wherein $R_1$ is selected from the group consisting of 2-(2-amino-4-thiazolyl)-2-(methoxyimino)acetamido-2-(2-amino-4-thiazolyl)- 2-(carboxymethoxyimino)acetamido, and 2-(2-amino-4-thiazolyl)-2-(hydroxyimino)acetamido.

16. The assay kit of claim 7 wherein $R_3$, $R_4$ and $R_5$ are independently selected from the group consisting of phenyl, p-iodophenyl, p-nitrophenyl, naphthyl, thiazolyl, alkylthiazolyl, benzothiazolyl, phthalylhydrazidyl, styryl, biphenyl, 3-biphenylene-2,5-diphenyltetrazolium chloride, 3-dimethoxy-4-biphenylene 2,5-diphenyltetrazolium chloride, 3-dimethoxy-4-biphenylene 2-p-nitrophenyl-5-phenyltetrazolium chloride and 3-dimethoxy-4-biphenylene-2,5-p-nitrophenyltetrazolium chloride.

17. An assay kit for the detection of ligand in a sample, comprising:
(a) a conjugate of a specific binding member to the ligand and a $\beta$-lactamase substrate of formula I:

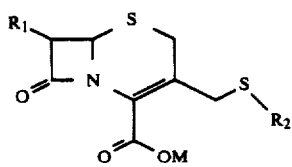

wherein $R_1$ is a group which maintains the ability of said substrate to be recognized as a substrate by $\beta$-lactamases and cleave the $\beta$-lactam ring; and $R_2$, together with the sulfur atom to which it is attached, form a leaving group which is released into solution, the conjugate acid of which has a pKa in water of less than 8, and M is hydrogen or a group I metal; and
(b) a tetrazolium salt of formula II:

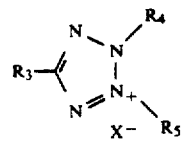

wherein $R_3$, $R_4$ and $R_5$ are independently selected from groups such that the redox potential of the resulting tetrazolium salt is 0 or lower volts; and X is an anion.

18. The assay kit of claim 17 further comprising an accelerator.

19. The assay kit of claim 18 wherein said accelerator comprises phenazine methosulfate.

20. The assay kit of claim 17 wherein said leaving group is selected from the group consisting of an aliphatic or aromatic thiol; a halo or amino substituted thiophenol; hydroxy, halo, or amino substituted mercapto pyridines; aliphatic or aromatic thiolcarboxylic acids; a thiosulfonic acid; and a mercapto amino acid.

21. The assay kit of claim 17 wherein said leaving group is selected from the group consisting of 4-bromothiophenol; 4-aminothiophenol, 2-mercapto-3-pyridinol; thiolacetic acid; thiobenzoic acid; or cysteine.

22. The assay kit of claim 17 wherein $R_1$ is selected from the group consisting of amino, thiophene-2-acetamido, benzyl-2-acetamido, phenoxy-2-acetamido, D-2-aminoadipamido, 2-amino-2-phenylacetamido, tetrazolylacetamido, 4-pyridylthioacetamido, 2-(2-amino-4-thiazolyl)-2-(methoxyimino)acetamido-2-(2-amino-4-thiazolyl)-2-(carboxymethoxyimino)acetamido, and 2-(2-amino-4-thiazolyl)-2-(hydroxyimino)acetamido.

23. The assay kit of claim 17 wherein $R_3$, $R_4$ and $R_5$ are independently selected from the group consisting of phenyl, p-iodophenyl, p-nitrophenyl, naphthyl, thiazolyl, alkylthiazolyl, benzothiazolyl, phthalylhydrazidyl, styryl, biphenyl, 3-biphenylene-2,5 diphenyltetrazolium chloride, 3-dimethoxy-4-biphenylene-2,5-diphenyltetrazolium chloride, 3-dimethoxy-4-biphenylene-2-p-nitrophenyl-5-phenyltetrazolium chloride and 3-dimethoxy-4-biphenylene-2,5-p-nitrophenyltetrazolium chloride.

* * * * *

UNITED STATES PATENT AND TRADEMARK OFFICE
CERTIFICATE OF CORRECTION

PATENT NO. : 4,978,613

DATED : December 18, 1990

INVENTOR(S) : Christopher Bieniarz, et al.

It is certified that error appears in the above-identified patent and that said Letters Patent is hereby corrected as shown below:

In claim 21, line 4, change "or" to --and cysteine.--

Signed and Sealed this

Thirtieth Day of June, 1992

Attest:

DOUGLAS B. COMER

*Attesting Officer*    *Acting Commissioner of Patents and Trademarks*